(12) United States Patent
Buesseler et al.

(10) Patent No.: US 11,779,732 B2
(45) Date of Patent: *Oct. 10, 2023

(54) MEDICAL DEVICE SENSOR

(71) Applicant: St. Jude Medical International Holding S.à r.l., Luxembourg (LU)

(72) Inventors: Ryan Kenneth Buesseler, Bristow, VA (US); Troy T. Tegg, Elk River, MN (US)

(73) Assignee: ST JUDE MEDICAL INTERNATIONAL HOLDING S.À R.L., Luxembourg (LU)

( * ) Notice: Subject to any disclaimer, the term of this patent is extended or adjusted under 35 U.S.C. 154(b) by 141 days.

This patent is subject to a terminal disclaimer.

(21) Appl. No.: 17/325,564

(22) Filed: May 20, 2021

(65) Prior Publication Data
US 2021/0338981 A1 Nov. 4, 2021

Related U.S. Application Data

(63) Continuation of application No. 15/819,768, filed on Nov. 21, 2017, now Pat. No. 11,040,173.

(60) Provisional application No. 62/424,860, filed on Nov. 21, 2016.

(51) Int. Cl.
| | |
|---|---|
| *A61B 5/00* | (2006.01) |
| *A61M 25/01* | (2006.01) |
| *A61L 29/02* | (2006.01) |
| *A61B 5/06* | (2006.01) |

(52) U.S. Cl.
CPC ......... *A61M 25/0127* (2013.01); *A61B 5/062* (2013.01); *A61L 29/02* (2013.01); *A61M 2025/0166* (2013.01); *A61M 2205/0272* (2013.01)

(58) Field of Classification Search
CPC ..................... A61B 5/062; A61M 2025/0166
See application file for complete search history.

(56) References Cited

U.S. PATENT DOCUMENTS

| | | | |
|---|---|---|---|
| 6,484,049 B1 | 11/2002 | Seeley et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 2005/0283067 A1 | 12/2005 | Sobe | |
| 2008/0146942 A1 | 6/2008 | Dala-Krishna | |
| 2012/0149966 A1 | 6/2012 | Ludwin et al. | |
| 2012/0245457 A1 | 9/2012 | Crowley | |
| 2013/0137963 A1* | 5/2013 | Olson | G16H 20/40 600/534 |
| 2013/0272592 A1 | 10/2013 | Hoory et al. | |
| 2016/0276739 A1* | 9/2016 | Buesseler | A61B 5/06 |

\* cited by examiner

*Primary Examiner* — Joel F Brutus
(74) *Attorney, Agent, or Firm* — Billion & Armitage

(57) ABSTRACT

Various embodiments of the present disclosure can include a catheter. The catheter can include an elongate shaft that extends along a longitudinal axis. The elongate shaft can include a shaft proximal end and a shaft distal end. A magnetically permeable shaft strip can be disposed along a particular shaft length of the elongate shaft. The magnetically permeable shaft strip can longitudinally extend along the elongate shaft.

20 Claims, 10 Drawing Sheets

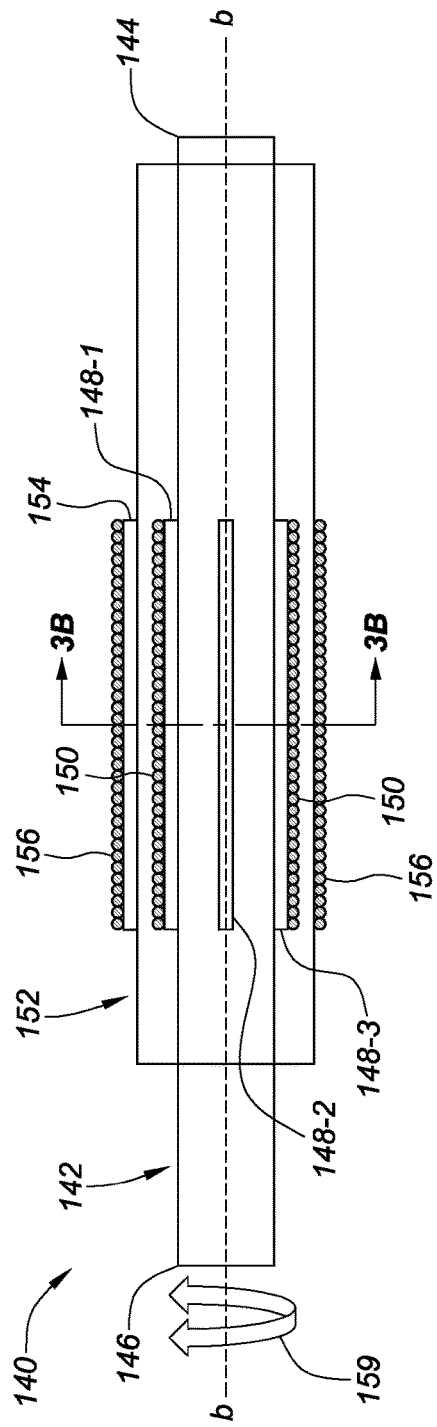
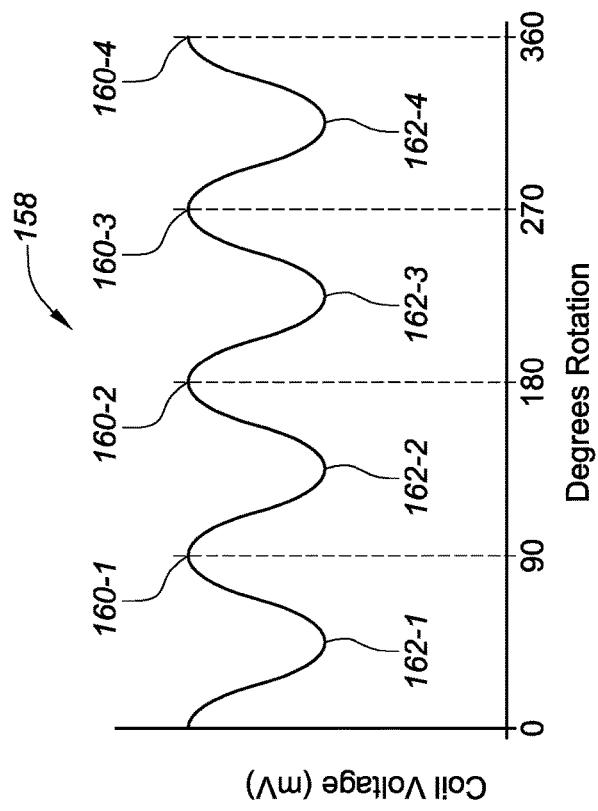
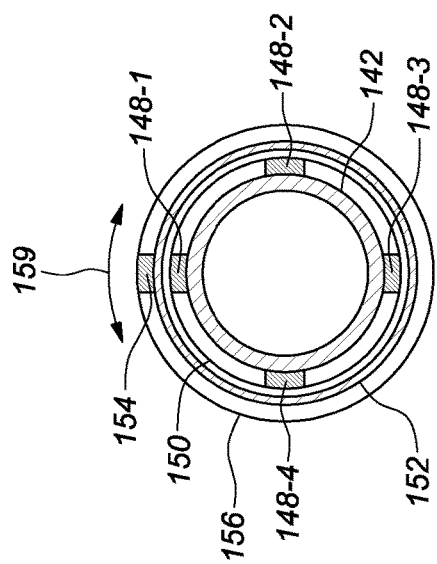

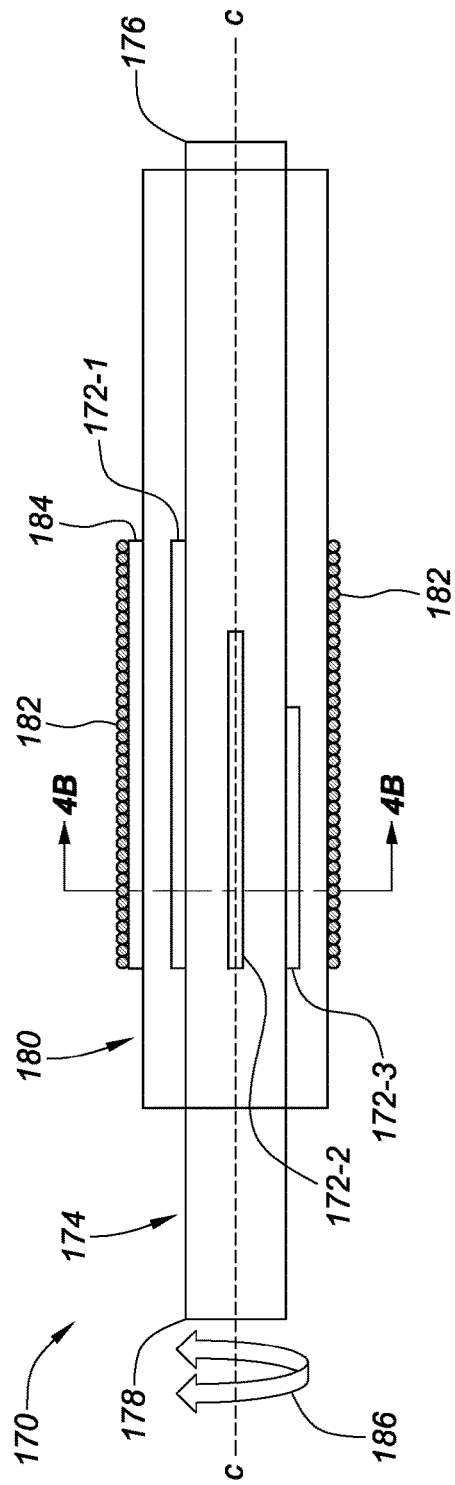
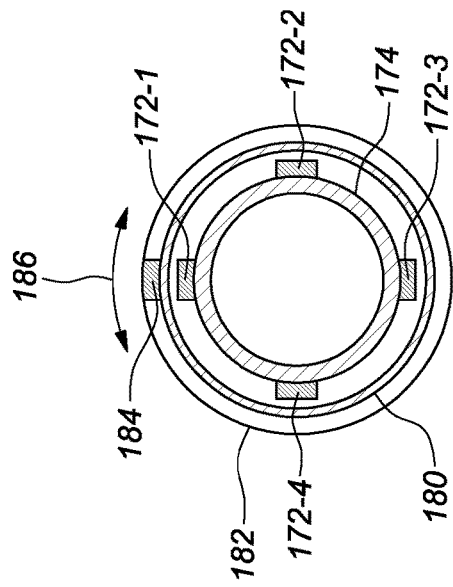
FIG. 4A
FIG. 4B

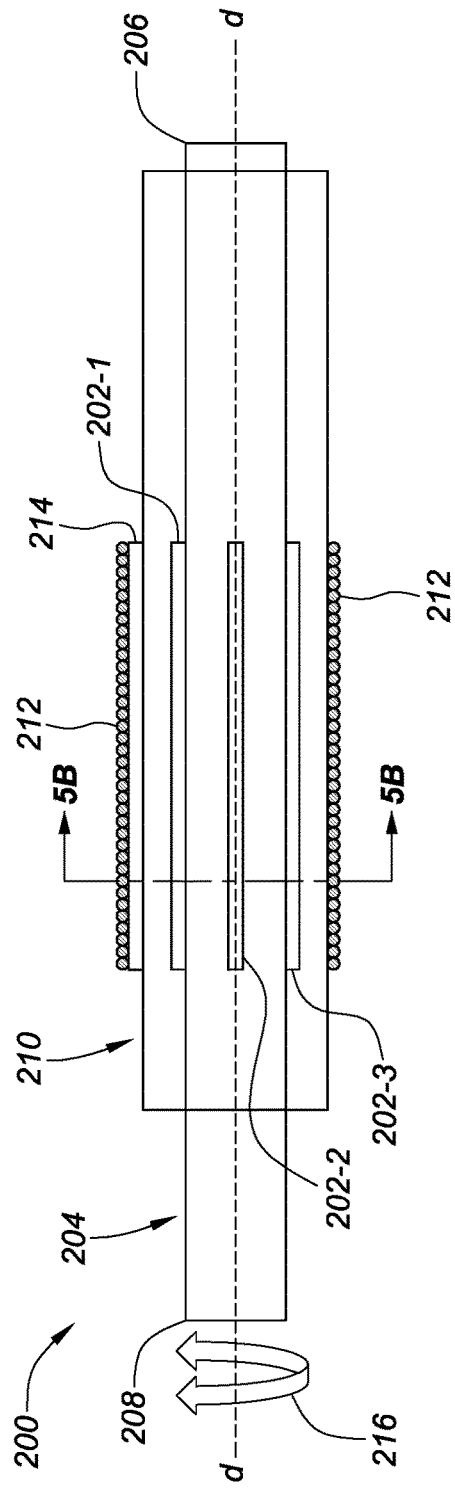
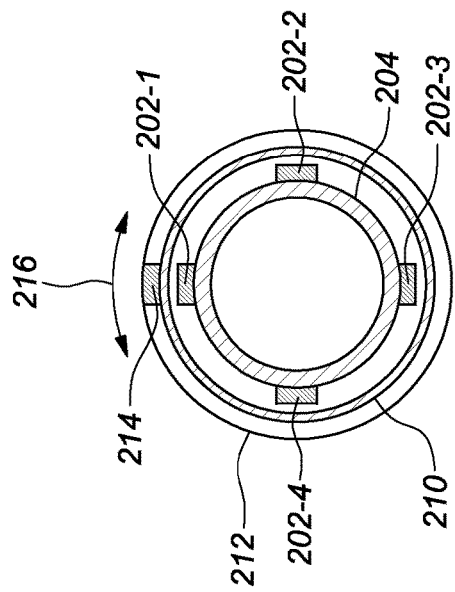

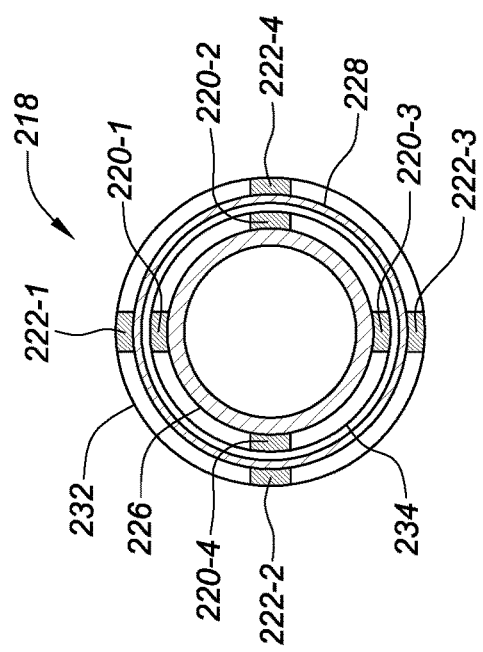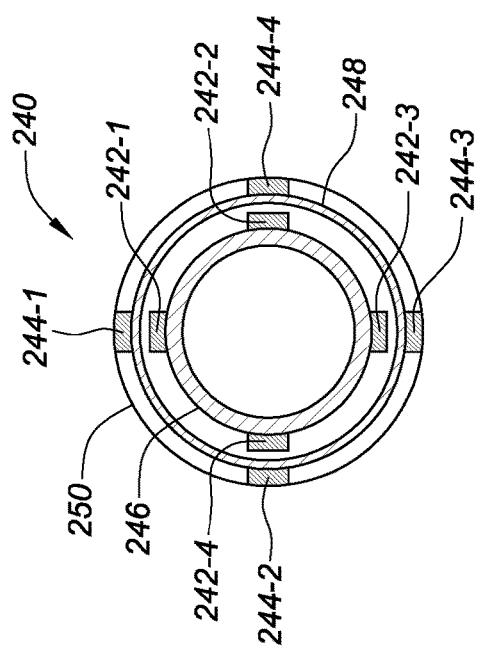

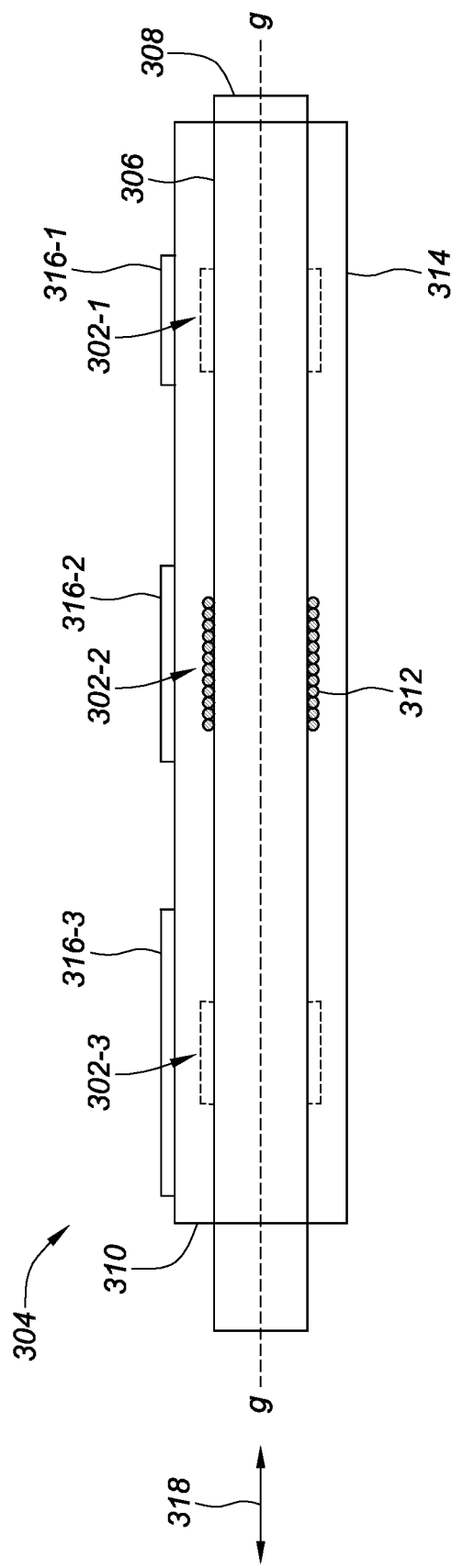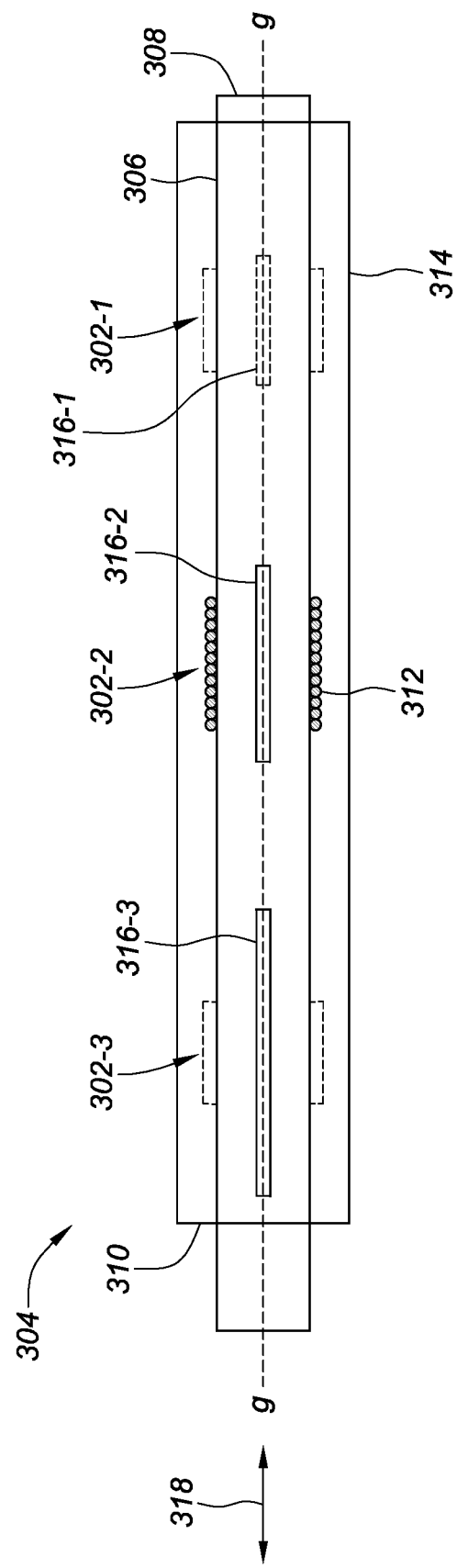

MEDICAL DEVICE SENSOR

CROSS-REFERENCE TO RELATED APPLICATIONS

This application is a continuation of U.S. application Ser. No. 15/819,768, filed 21 Nov. 2017 (the '768 application), which claims the benefit of U.S. provisional application No. 62/424,860, filed 21 Nov. 2016 (the '860 application). The '768 application, and '860 application are both hereby incorporated by reference as though fully set forth herein.

BACKGROUND a. Field

The present disclosure relates generally to a sensor for a medical device.

b. Background

Medical devices such as guidewires, catheters, introducers and the like that include electromagnetic coil position sensors or electrodes for device navigation are used in various medical procedures in the body. For example, it is known to equip a catheter with multiple coils sufficient to allow a position sensing system to detect six (6) degrees-of-freedom (DOF), namely, a three-dimensional (3D) position (X, Y, Z) and a 3D orientation (e.g., roll, pitch, yaw) thereof. However, the design of a coil assembly that can provide such functionality provides challenges, particularly with respect to space constraints.

One known electromagnetic position sensor includes a coil wound symmetrically on a tubular core. Such a sensor may be seen by reference to U.S. Pat. No. 7,197,354, entitled "System for Determining the Position and Orientation of a Catheter" issued to Sobe, hereby incorporated by reference in its entirety as though fully set forth herein. Sobe discloses a core that is hollow, is symmetric about a central axis, and can be scaled in length, inner diameter, and outer diameter for a particular application. A coil is wound on the core in a desired winding pattern. The coil, like the core, is symmetric about the central axis. The sensor can be used in a system to detect position in 3D space defined by three perpendicular axes (X, Y, and Z), as well as rotation about two of the three axes (e.g., pitch and yaw), but the coil cannot detect rotation about the central axis of the core (e.g., roll). Accordingly, a medical device that incorporates a single sensor coil mounted symmetric about the central axis of the medical device only senses five (5) DOF, that is, two orientation parameters, in addition to three position parameters. Despite the DOF limitation, there are nonetheless desirable aspects of the above configuration. For example, the configuration uses minimal space and accommodates an open central lumen.

SUMMARY

Various embodiments of the present disclosure can include a catheter. The catheter can include an elongate shaft that extends along a longitudinal axis. The elongate shaft can include a shaft proximal end and a shaft distal end. A magnetically permeable shaft strip can be disposed along a particular shaft length of the elongate shaft. The magnetically permeable shaft strip can longitudinally extend along the elongate shaft.

Various embodiments of the present disclosure can include an introducer. The introducer can include an elongate sheath extending along a sheath longitudinal axis. The elongate sheath can include a sheath proximal end and a sheath distal end. The elongate sheath can include a central lumen that extends therethrough along the sheath longitudinal axis.

Various embodiments of the present disclosure can include a kit. In some embodiments, the kit can include a catheter comprising an elongate shaft extending along a shaft longitudinal axis and including a shaft proximal end and a shaft distal end. A magnetically permeable shaft strip can be disposed along a particular shaft length of the elongate shaft. In some embodiments, the kit can include an introducer comprising an elongate sheath extending along a sheath longitudinal axis and including a sheath proximal end and a sheath distal end. The elongate sheath can include a central lumen through which the elongate shaft is configured to pass. A magnetically permeable sheath strip can be disposed along a particular sheath length of the elongate sheath.

BRIEF DESCRIPTION OF THE DRAWINGS

FIG. 3A is a schematic cross-sectional side view of a dual sensor medical device with magnetically permeable shaft strips of a same length, in accordance with embodiments of the present disclosure.

FIG. 3B is a cross-sectional end view of the dual sensor medical device depicted in FIG. 3B along line 3B-3B, in accordance with embodiments of the present disclosure.

FIG. 3C is a graph that illustrates a coil voltage with respect to a rotation of a portion of the single sensor medical device depicted in FIGS. 3A and 3B, in accordance with embodiments of the present disclosure.

FIG. 4A is a schematic cross-sectional side view of a single sensor medical device with variable length magnetically permeable shaft strips, in accordance with embodiments of the present disclosure.

FIG. 4B is a cross-sectional end view of the single sensor medical device depicted in FIG. 4A along line 4B-4B, in accordance with embodiments of the present disclosure.

FIG. 5A is a schematic cross-sectional side view of a single sensor medical device with magnetically permeable shaft strips of a same length, in accordance with embodiments of the present disclosure.

FIG. 5B is a cross-sectional end view of the single sensor medical device depicted in FIG. 5A along line 5B-5B, in accordance with embodiments of the present disclosure.

FIG. 6A is a cross-sectional end view of a dual sensor medical device with an equal number of magnetically permeable shaft strips and sheath strips, in accordance with embodiments of the present disclosure.

FIG. 6B is a cross-sectional end view of a single sensor medical device with an equal number of magnetically permeable shaft strips and sheath strips, in accordance with embodiments of the present disclosure.

FIG. 9A is a partial cross-sectional side view of a single sensor medical device for sensing a linear movement of a portion of the medical device with a plurality of magnetically permeable sheath strips, in accordance with embodiments of the present disclosure.

FIG. 9B is a partial cross-sectional top view of a single sensor medical device for sensing a linear movement of a portion of the medical device with a plurality of magnetically permeable sheath strips, in accordance with embodiments of the present disclosure.

DETAILED DESCRIPTION

Figure 1:
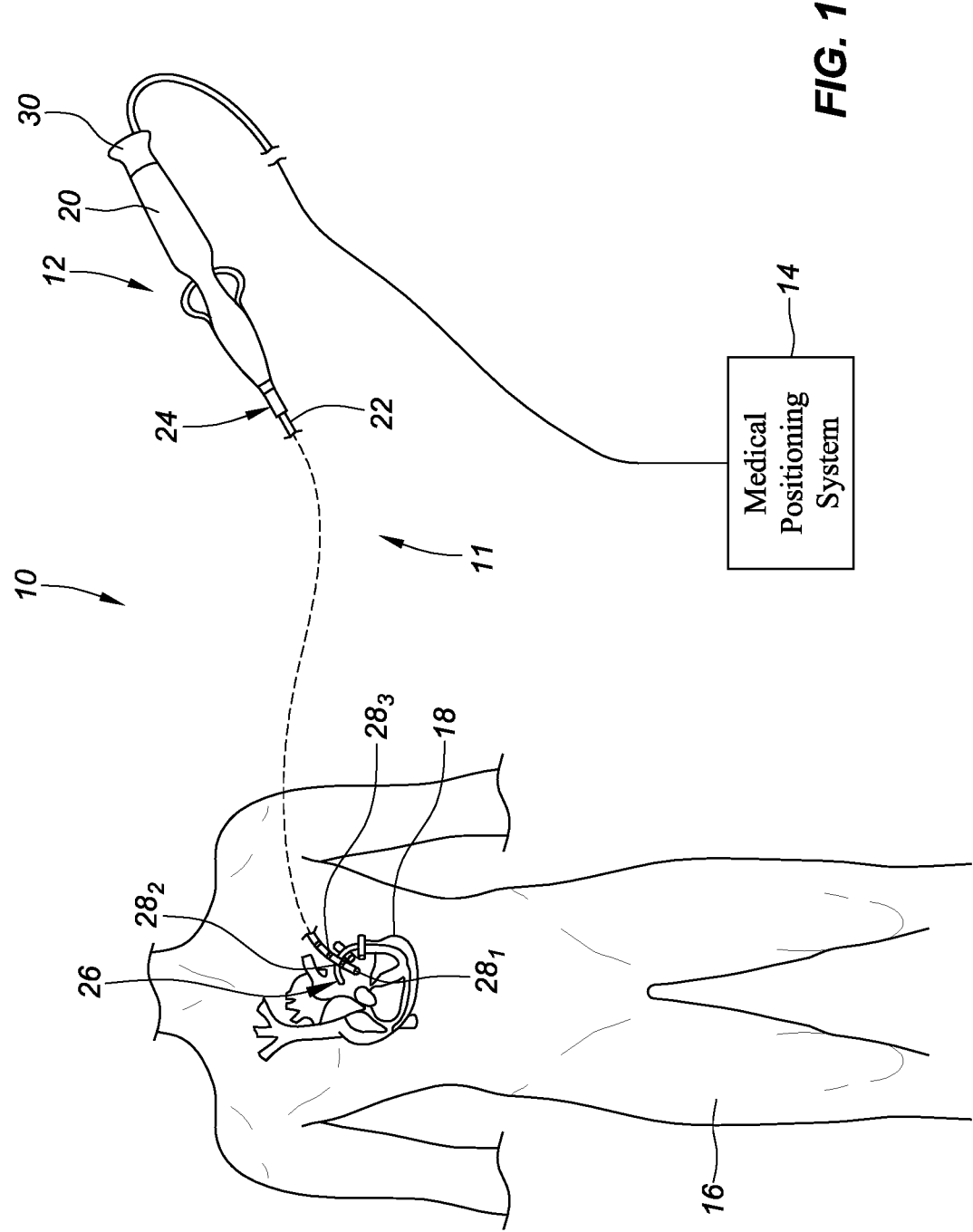
FIG. 1 depicts a diagrammatic view of an exemplary system for performing one or more diagnostic or therapeutic procedures, wherein the system comprises a magnetic field-based medical positioning system, in accordance with embodiments of the present disclosure.

FIG. 1 depicts a diagrammatic view of an exemplary system 10 for performing one or more diagnostic or therapeutic procedures, wherein the system 10 comprises a magnetic field-based medical positioning system, in accordance with embodiments of the present disclosure. In some embodiments, and with reference to FIG. 1, the system 10 can include a medical device 11 and a medical positioning system 14. The medical device 11 can include an elongate medical device such as, for example, a catheter or a sheath. For purposes of illustration and clarity, the description below will be limited to an embodiment wherein the medical device 11 comprises a catheter (e.g., catheter 12). It will be appreciated, however, that the present disclosure is not meant to be limited to such an embodiment, but rather in other exemplary embodiments, the medical device may comprise other elongate medical devices, such as, for example and without limitation, sheaths, introducers and the like.

With continued reference to FIG. 1, the catheter 12 can be configured to be inserted into a patient's body 16, and more particularly, into the patient's heart 18. The catheter 12 may include a handle 20 that has a proximal end 30, a shaft 22 having a proximal end portion 24 and a distal end portion 26, and one or more sensors 28 mounted in or on the shaft 22 of the catheter 12. As used herein, "sensor 28" or "sensors 28" may refer to one or more sensors $28_1$, $28_2$, ... $28_N$, as appropriate and as generally depicted. In an exemplary embodiment, the sensors 28 are disposed at the distal end portion 26 of the shaft 22. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The shaft 22 can be an elongate, tubular, flexible member configured for movement within the body 16. The shaft 22 supports, for example and without limitation, sensors and/or electrodes mounted thereon, such as, for example, the sensors 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and define one or more lumens configured to house and/or transport electrical conductors, fluids, and/or surgical tools. The shaft 22 may be introduced into a blood vessel or other structure within the body 16 through a conventional introducer. The shaft 22 may then be steered or guided through the body 16 to a desired location, such as the heart 18, using means well known in the art.

The sensors 28 mounted in or on the shaft 22 of the catheter 12 may be provided for a variety of diagnostic and therapeutic purposes including, for example and without limitation, electrophysiological studies, pacing, cardiac mapping, and ablation. In an exemplary embodiment, one or more of the sensors 28 are provided to perform a location or position sensing function.

In some embodiments, one or more of the sensors 28 can be an electromagnetic position sensor, such as a wound coil, which can sense a magnetic field that is generated in proximity to the patient. Depending on a position and orientation (P&O) of the electromagnetic position sensor, different electrical signals can be generated by the coil and transferred to the medical positioning system 14, for a determination of a location reading that can be indicative of the P&O of the sensor 28.

The location readings may each include at least one or both of a position and an orientation (P&O) relative to a reference coordinate system, which may be the coordinate system of medical positioning system 14. For some types of sensors, the P&O may be expressed with five degrees-of-freedom (five DOF) as a three-dimensional (3D) position (i.e., a coordinate in three axes X, Y and Z) and two-dimensional (2D) orientation (e.g., an azimuth and elevation) of sensor 28 in a magnetic field relative to a magnetic field generator(s) or transmitter(s) and/or a plurality of electrodes in an applied electrical field relative to an electrical field generator (e.g., a set of electrode patches). For other sensor types, the P&O may be expressed with six degrees-of-freedom (six DOF) as a 3D position (i.e., X, Y, Z coordinates) and 3D orientation (i.e., roll, pitch, and yaw).

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Figure 2A:
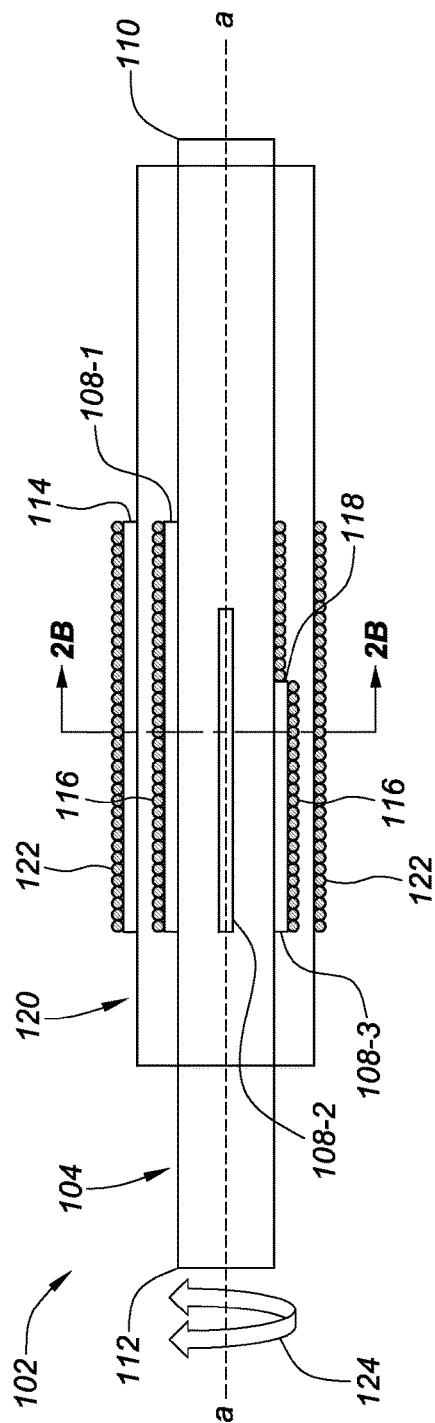
FIG. 2A is a schematic side view of a dual sensor medical device with variable length magnetically permeable shaft strips, in accordance with embodiments of the present disclosure.
Figure 2C:
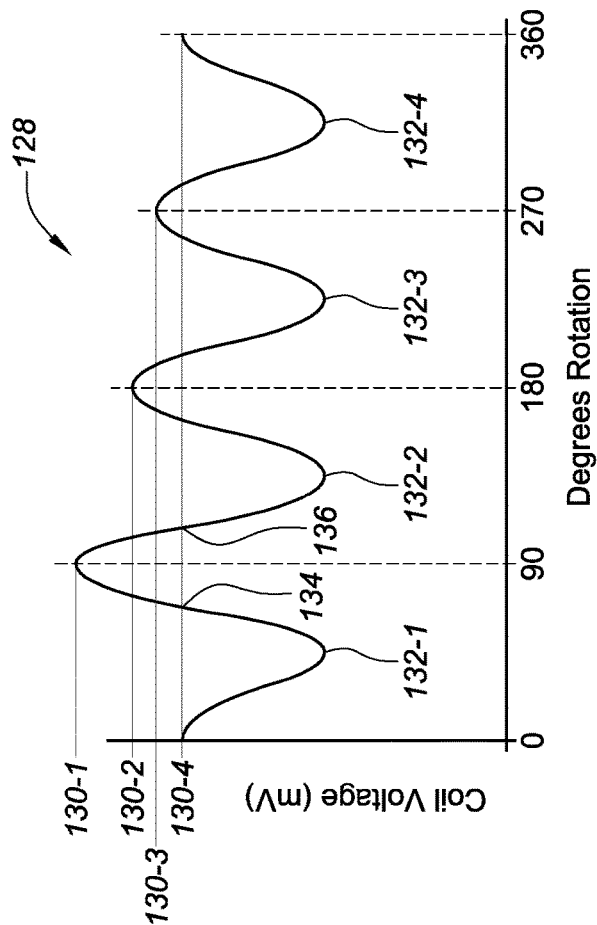
FIG. 2C is a graph that illustrates a coil voltage model with respect to a rotation of a portion of the dual sensor medical device depicted in FIGS. 2A and 2B, in accordance with embodiments of the present disclosure.
Figure 2B:
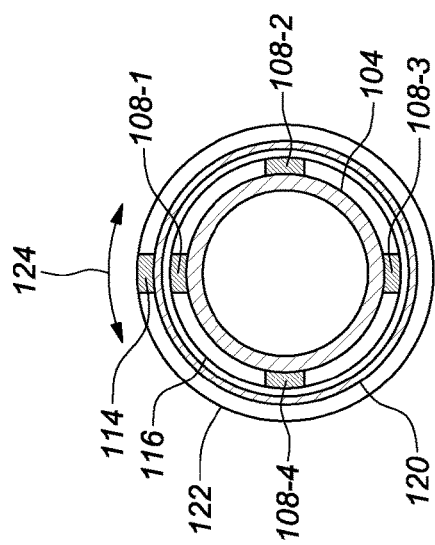
FIG. 2B is a cross-sectional end view of the dual sensor medical device depicted in FIG. 2A along line 2B-2B, in accordance with embodiments of the present disclosure.

FIG. 2A is a schematic side view of a dual sensor medical device 102 with variable length magnetically permeable shaft strips 108-1, 108-2, 108-3 and FIG. 2B is a cross-sectional end view of the dual sensor medical device depicted in FIG. 2A along line 2B-2B, in accordance with embodiments of the present disclosure. Although the present disclosure refers to a medical device 102, embodiments of the present disclosure can include two separate medical devices. For example, embodiments of the present disclosure can include an elongate shaft 104 (e.g., catheter) and an elongate sheath 120, further discussed herein. In some embodiments, the elongate shaft 104 can extend along a shaft longitudinal axis a-a and can include a shaft proximal end 110 and a shaft distal end 112. Although the elongate shaft 104 (e.g., catheter) is discussed as being a shaft herein, in some embodiments, the elongate shaft 104 can be a sheath or other type of elongate medical device. In some embodiments, the shaft 104 can be hollow or solid and/or can include additional components. For example, the shaft 104 can include items such as pull wires, conductors, optical fibers, etc.

In some embodiments, one or more magnetically permeable shaft strips 108-1, 108-2, 108-3 can be disposed along a particular shaft length of the elongate shaft 104 and are hereinafter referred to in the plural as magnetically permeable shaft strips 108. The elongate shaft 104 includes a fourth magnetically permeable shaft strip, which is further depicted in FIG. 2B. The elongate shaft 104 can include fewer than or greater than four magnetically permeable shaft strips 108, in some embodiments. As depicted, a first magnetically permeable shaft strip 108-1 is disposed on top of the elongate shaft 104 and a third magnetically permeable shaft strip 108-3 is disposed on the elongate shaft 104 diametrically opposed from the first magnetically permeable shaft strip 108-1. In some embodiments, a second magnetically permeable shaft strip 108-2 is disposed on a side of the elongate shaft 104. For example, the second magnetically permeable shaft strip 108-2 is disposed on the elongate shaft 104, 90 degrees opposed to the first magnetically permeable shaft strip 108-1 and the third magnetically permeable shaft strip 108-3. In some embodiments, the fourth magnetically permeable shaft strip can be diametrically opposed to the second magnetically permeable shaft strip 108-2 and can be disposed on the elongate shaft 104, 90 degrees opposed to the first magnetically permeable shaft strip 108-1 and the third magnetically permeable shaft strip 108-3.

In an example, the magnetically permeable shaft strips 108 can be circumferentially disposed about the elongate shaft 104. In some embodiments, as depicted in FIG. 2A, the magnetically permeable shaft strips 108 can be equally spaced about the elongate shaft 104. For example, a circumferential spacing between each of the magnetically permeable shaft strips 108 can be equal to one another. Alternatively, the circumferential spacing between each of the magnetically permeable shaft strips 108 can vary.

Each of the magnetically permeable shaft strips 108 can be of a different length, in some embodiments. For example, the first magnetically permeable shaft strip 108-1 can be of a first length, which is longer than the second, third, and fourth magnetically permeable shaft strips 108. The second magnetically permeable shaft strip 108-2 can be of a second length, which can be less than the first length, the third magnetically permeable shaft strip 108-3 can be of a third length, which can be less than the second length, and the fourth magnetically permeable shaft strip 108-4 can be of a fourth length that is less than the third length. As such, a longitudinal length of each of the plurality of magnetically permeable shaft strips decreases or increases in a first circumferential direction.

In some embodiments, as depicted, a distal end of each of the magnetically permeable shaft strips 108 can be disposed at a same longitudinal length along the shaft longitudinal axis a-a and the proximal ends of each of the magnetically permeable shaft strips 108 can be disposed at varied longitudinal lengths. In some embodiments, a proximal end of each of the magnetically permeable shaft strips 108 can be disposed at a same longitudinal length along the shaft longitudinal axis a-a and the distal ends of each of the magnetically permeable shaft strips 108 can be disposed at varied longitudinal lengths along the shaft longitudinal axis a-a. In some embodiments, each of the magnetically permeable shaft strips 108 can be centered with respect to a particular point along the shaft longitudinal axis a-a. For example, the second magnetically permeable shaft strip 108-2 can be centered between the proximal and distal end of the first magnetically permeable shaft strip 108-1; the third magnetically permeable shaft strip 108-3 can be centered between the proximal and distal end of the second magnetically permeable shaft strip 108-2; and the fourth magnetically permeable shaft strip 108-4 can be centered between the proximal and distal end of the third magnetically permeable shaft strip 108-3.

In some embodiments, although each of the magnetically permeable shaft strips 108 are depicted as being formed from a unitary piece of material, each of the magnetically permeable shaft strips 108 can be formed from a plurality of traces, which together form each of the magnetically permeable shaft strips 108. For example, each of the magnetically permeable shaft strips 108 can be formed by a plurality of longitudinally spaced apart magnetically permeable traces that are aligned with the longitudinal axis a-a.

In some embodiments, the elongate shaft 104 can include a shaft sensor 116 disposed along a portion of the particular shaft length that the magnetically permeable shaft strips 108 are disposed. The shaft sensor 116 can be a wound coil in some embodiments. For example, the shaft sensor 116 can be formed from a wire, which is wound around an outer surface of the elongate shaft 104 and along the shaft longitudinal axis a-a. In some embodiments, as depicted, the magnetically permeable shaft strips 108 can be disposed between an inner surface of the elongate shaft 104 and an inner surface of the shaft sensor 116.

In some embodiments, the elongate shaft 104 can define one or more lumens in a wall of the elongate shaft 104, which travel longitudinally and parallel with the longitudinal axis a-a of the elongate shaft 104. For example, the elongate shaft 104 can include a quad-lumen with pairs of diametrically opposed lumens that are disposed in the wall of the elongate shaft 104. In some embodiments, the magnetically permeable shaft strips 108 can be disposed in each one of the lumens that are disposed in the wall of the elongate shaft 104. In some embodiments, the magnetically permeable shaft strips 108 can be incorporated into a braid associated with the elongate shaft 104, as further discussed in relation to U.S. patent application Ser. No. 15/072,185, which is hereby incorporated by reference as though fully set forth herein. In some embodiments, the magnetically permeable shaft strips 108 can be disposed between an outer surface of the elongate shaft 104 and the inner surface of the shaft sensor 116, such that the shaft sensor 116 surrounds the magnetically permeable strips 108 and the particular portion of the outer surface of the elongate shaft 104.

A thickness of the magnetically permeable shaft strips 108 can be in a range from 5 microns to 25 microns, in some embodiments, although the thickness of the magnetically permeable shaft strips 108 can be less than 5 microns or greater than 25 microns in some embodiments. In some embodiments, the thickness of the magnetically permeable shaft strips 108 can be in a range from 10 microns to 20 microns and preferably can be approximately 15 microns. Although a sensor transition step 118 is depicted in FIG. 2A where wire forming the shaft sensor transitions from being wound around the magnetically permeable shaft strip 108 to being wound around an outer surface of the elongate shaft 104, the sensor transition step 118 can be reduced as a result of the relatively small thickness of the magnetically permeable strips 108-3. In some embodiments, the sensor transition step 118 can be removed altogether if a material with a lesser magnetic permeability than the magnetically permeable shaft strip 108-3 is placed in longitudinal series with the magnetically permeable shaft strip 108-3; such that the shaft sensor 116 is wound at the same diameter next to the magnetically permeable shaft strip 108-3. In some embodiments, the magnetically permeable strips 108 can be disposed within lumens that extend through the wall of the elongate shaft 104, as discussed herein, and/or can be disposed within longitudinal channels formed in an outer and/or inner surface of the elongate shaft 104.

Embodiments of the present disclosure can include an elongate sheath 120 that extends along a sheath longitudinal axis. In some embodiments, the sheath longitudinal axis can be generally parallel with the shaft longitudinal axis a-a and/or coincident with the shaft longitudinal axis a-a. The elongate sheath 120 can include a central lumen through which the elongate shaft 104 passes. For example, the central lumen of the elongate sheath can be sized and configured to pass a medical device therethrough. In some embodiments, the elongate shaft 104 can be moved longitudinally through the central lumen of the elongate sheath 120 and/or rotated within the central lumen of the elongate sheath 120.

The elongate sheath 120 can include a magnetically permeable sheath strip 114 disposed along a particular sheath length of the elongate sheath 120, which can be formed from a magnetically permeable material that is the same or different from the magnetically permeable material that forms the magnetically permeable shaft strip 108. In an example, the magnetically permeable material that forms the magnetically permeable sheath strip 114 and/or the magnetically permeable shaft strip 108 can include one or more of the following: ferrite, martensitic stainless steel, ferritic stainless steel, electrical steel, iron, permalloy, cobalt-iron, mu-metal, metallic glass (e.g., Metglas®), nickel, etc. In some embodiments, the magnetically permeable material can have a magnetic permeability greater than 10 Henries per meter (H/m). In some embodiments, the magnetically permeable sheath strip 114 can have a length that is greater than, equal to, or less than a length of the longest magnetically permeable shaft strip 108. In some embodiments, a sheath sensor 122 can be disposed along a portion of the particular sheath length. The particular shaft length and the particular sheath length can overlap in some embodiments, depending on where the elongate shaft 104 is linearly disposed along the longitudinal axis a-a with respect to the elongate sheath 120. For example, the elongate shaft 104 can be pushed proximally and/or distally (e.g., protracted/retracted) with respect to the elongate sheath 120.

The sheath sensor 122 can include a coil extending along and disposed about the sheath longitudinal axis and can be disposed along a portion of the elongate sheath 120. In some embodiments, the sheath sensor can be disposed along a distal portion of the elongate sheath 120, a proximal portion of the elongate sheath 120, or a portion of the elongate sheath 120 between a proximal and distal end of the elongate sheath 120. In some embodiments, the magnetically permeable sheath strip 114 can be disposed between an inner surface of the elongate sheath 120 and the coil. For example, as discussed in relation to the magnetically permeable shaft strips 108, the magnetically permeable sheath strip 114 can be disposed in an elongate lumen extending through a wall of the elongate sheath 120. For example, the elongate sheath 120 can include a quad-lumen, as discussed in relation to the elongate shaft 104, in which the magnetically permeable sheath strips 114 can be disposed. In some embodiments, the magnetically permeable sheath strips 114 can be incorporated into a braid associated with the elongate sheath 120, as further discussed in relation to U.S. patent application Ser. No. 15/072,185, which is hereby incorporated by reference as though fully set forth herein. In some embodiments, the magnetically permeable sheath strip 114 can be disposed between the coil of the magnetic sheath sensor 122 and an outer surface of the elongate sheath 120 and/or can be disposed within longitudinal channels formed in an outer and/or inner surface of the elongate shaft 104.

The sheath sensor 122 can be configured to detect a rotation of the elongate shaft 104 based on a rotation of the magnetically permeable shaft strips 108 relative to the magnetically permeable sheath strips 114. For example, the elongate sheath 120 can be used as an introducer to provide an access point and allow the insertion of instruments (e.g., the elongate shaft 104 or other medical device) into a lumen (e.g., vein, artery, etc.). The elongate shaft 104 can be rotated within the elongate sheath 120 and/or protracted/retracted within the elongate shaft 120 to provide an instrument disposed on a tip of the elongate shaft 104 with better access to a particular site where a medical procedure is being performed. In some prior methods, a sensor can be placed on the elongate shaft 104 that provides 6 DOF sensing expressed as 3D position (i.e., X, Y, Z coordinates) and 3D orientation (i.e., roll, pitch, and yaw). However, the design of these sensors can be of an increased complexity and can occupy valuable real estate in the elongate shaft 104.

Embodiments of the present disclosure can detect a rotation of the elongate shaft 104 based on a rotation of the magnetically permeable shaft strips 108 relative to the magnetically permeable sheath strips 114. For example, the sheath sensor 122 disposed along the portion of the particular sheath length can be configured to detect a rotation of the elongate shaft 104 based on a rotation of the magnetically permeable shaft strips 108 relative to the magnetically permeable sheath strips 114. Upon rotation of the elongate shaft 104 with respect to elongate sheath 120, the magnetically permeable shaft strips 108 are also rotated with respect to the magnetically permeable sheath strips 114. With respect to the shaft sensor 116, the magnetically permeable strips 108 can cause an increased magnetic field interaction with the shaft sensor 116, as further discussed in relation to U.S. patent application Ser. No. 15/072,185, which is hereby incorporated as though fully set forth herein. In an example, the magnetically permeable shaft strips 108 can provide a path through which a magnetic field can flow, thus concentrating a magnetic flux into shaft sensor 116, which can increase a current generated within the coil winding of the sheath sensor 122.

Similarly, the magnetically permeable sheath strips 114 can concentrate a magnetic flux into sheath sensor 122, thus increasing a current generated within the coil winding of the sheath sensor 122. As the elongate shaft 104 is rotated with respect to the elongate sheath 120 in a direction of arrow 124, over the course of the rotation of the elongate shaft 104, each of the magnetically permeable shaft strips 108 can be aligned (e.g., overlap) with the magnetically permeable sheath strips 114. As each one of the magnetically permeable shaft strips 108 is aligned with the magnetically permeable sheath strips 114, a mass of high permeability material becomes concentrated due to the alignment of the two magnetically permeable strips. Thus, an increased concentration of magnetic flux can be delivered into the shaft sensor 116 and/or the sheath sensor 122. The increased concentration of magnetic flux delivered into the shaft sensor 116 and/or the sheath sensor 122 can cause an increased current to be generated within the coil winding of the shaft sensor 116 and/or sheath sensor 122, as depicted in FIG. 2C.

FIG. 2C is a graph that illustrates a coil voltage model 128 with respect to a rotation of a portion of the dual sensor medical device 102 depicted in FIGS. 2A and 2B, in accordance with embodiments of the present disclosure. As depicted in FIG. 2A, each of the magnetically permeable shaft strips 108 can vary in length, resulting in different masses of magnetically permeable material being placed within a proximity of the shaft sensor 116 and the sheath sensor 122. In an example, the differing masses of magnetically permeable material being placed within a proximity of the shaft sensor 116 and the sheath sensor 122 can create an asymmetric concentration of the magnetic field, thereby causing the below effect. In an example, a current generated within coil windings of the shaft sensor 116 and the sheath sensor 122 can vary as the coils and strips are rotated in proximity to each other and overlap one another, as depicted in FIG. 2C. For instance, a first coil voltage maximum 130-1 can be associated with the first magnetically permeable shaft strip 108-1 being radially aligned with the magnetically permeable sheath strip 114. As the elongate shaft 104 is rotated within the elongate sheath 120, various other ones of the magnetically permeable shaft strips 108 can be radially aligned with the magnetically permeable sheath strip 114, causing differing voltages to be generated by the sheath sensor 122. For example, when the second magnetically permeable shaft strip 108-2 becomes radially aligned with the magnetically permeable sheath strip 114, a second coil voltage 130-2 can be generated by the sheath sensor 122; when the third magnetically permeable shaft strip 108-3 becomes radially aligned with the magnetically permeable sheath strip 114, a third coil voltage 130-3 can be generated by the sheath sensor 122; and when the fourth magnetically permeable shaft strip 108-4 becomes radially aligned with the magnetically permeable sheath strip 114, a fourth coil voltage 130-4 can be generated by the sheath sensor 122.

As previously discussed, the second magnetically permeable shaft strip 108-2 can be shorter than the first magnetically permeable shaft strip 108-1, the third magnetically permeable shaft strip 108-3 can be shorter than the second magnetically permeable shaft strip 108-2, and the fourth magnetically permeable shaft strip 108-4 can be shorter than the third magnetically permeable shaft strip 108-3. As a result, a mass of high permeability material that is placed in close proximity to the sheath sensor 122 can be varied as each magnetically permeable shaft strip 108 becomes radially aligned (e.g., overlaps) with the magnetically permeable sheath strip 114. For example, the mass of high permeability material placed in close proximity to the sheath sensor 122 can be varied between the first, second, third, and fourth magnetically permeable shaft strips 108.

In some embodiments, a particular roll of the elongate shaft 104 (e.g., rotation of the elongate shaft 104 with respect to the elongate sheath 120) can be determined based on the coil voltage generated by the sheath sensor 122. For instance, a determination can be made that the elongate shaft 104 has been rotated 90 degrees with respect to the elongate sheath 120 in response to a first coil voltage maximum 130-1 being generated by the sheath sensor 122; 180 degrees with respect to the elongate sheath 120 in response to a second coil voltage maximum 130-2 being generated by the sheath sensor 122; 270 degrees with respect to the elongate sheath 120 in response to a third coil voltage maximum 130-3 being generated by the sheath sensor 122; and 360 degrees with respect to the elongate sheath 120 in response to a fourth coil voltage maximum 130-4 being generated by the sheath sensor 122. In some embodiments, when a voltage generated by the sheath sensor 122 is in a range between the first coil voltage maximum 130-1 and the second coil voltage maximum 130-2, a determination can be made that the elongate shaft has rotated within a particular range of 90 degrees. When a voltage generated by the sheath sensor is in a range between the second coil voltage maximum 130-2 and the third coil voltage maximum 130-3, a determination can be made that the elongate shaft 104 has rotated within a particular range of 180 degrees. Similarly, when a voltage generated by the sheath sensor is in a range between the third coil voltage maximum 130-3 and the fourth coil voltage maximum 130-4, a determination can be made that the elongate shaft has rotated within a particular range of 270 degrees.

In some embodiments, a particular degree of rotation of the elongate shaft 104 with respect to the elongate sheath 120 can be determined. For example, a particular degree of rotation between 0 to 90 degrees, between 90 to 180 degrees, between 180 to 270 degrees, and/or between 270 to 360 degrees can be determined. For example, when the elongate shaft 104 is rotated between 0 to 90 degrees with respect to the elongate sheath 120, a first coil voltage minimum 132-1 is produced by the sheath sensor 122 when the elongate shaft 104 is rotated to approximately 45 degrees; a second coil voltage minimum 132-2 is produced by the sheath sensor 122 when the elongate shaft 104 is rotated to approximately 135 degrees; a third coil voltage minimum 132-3 is produced by the sheath sensor 122 when the elongate shaft 104 is rotated to approximately 225 degrees; and a fourth coil voltage minimum 132-4 is produced by the sheath sensor 122 when the elongate shaft 104 is rotated to approximately 315 degrees.

In some embodiments, a same coil voltage can be produced by the sheath sensor 122 at various degrees of rotation of the elongate shaft 104 with respect to the elongate sheath 120. For instance, a coil voltage that is equivalent to the fourth coil voltage maximum 130-4 can also be produced by the sheath sensor 122 where the peaks associated with the first coil voltage maximum 130-1, second coil voltage maximum 130-2, and third coil voltage maximum 130-3 intersect the coil voltage associated with the fourth voltage maximum 130-4. Thus, the sheath sensor 122 can produce a same voltage at degrees of rotation that are less than and greater than 90 degrees, less than and greater than 180 degrees, less than and greater than 270 degrees, and at 360 degrees of rotation. Accordingly, to differentiate between the voltages produced by the sheath sensor 122 at the various degrees of rotation, a voltage model can be derived (e.g., empirically or theoretically) in relation to the various voltages produced by the sheath sensor 122, as the sheath sensor is rotated.

When a duplicative voltage is encountered upon rotation of the elongate shaft 104 with respect to the elongate sheath 120, such as first duplicative voltage 134, which can be the same as the fourth voltage maximum 130-4 and/or can be within a defined range of fourth voltage maximum 130-4; surrounding voltages associated with various degrees of rotation can be analyzed to determine a particular degree of rotation associated with the first duplicative voltage 134. For instance, when the first duplicative voltage 134 is produced by the sheath sensor 122, surrounding voltages can be analyzed to determine the degree of rotation of the elongate shaft 104 within the elongate sheath 120. In an example, if the surrounding voltage reaches a maximum voltage, such as first voltage maximum 130-1 and/or a voltage that exceeds second voltage maximum 130-2, a determination can be made that the degree of rotation is associated with the first duplicative voltage 134 or a second duplicative voltage 136 because both the first duplicative voltage 134 and the second duplicative voltage 136 surround the voltage peak associated with the first voltage maximum. Because the peak associated with the first voltage maximum includes at least two duplicative voltages 134, 136, distinguishing between the degree of rotation associated with the duplicative voltages 134, 136 can be difficult. For example, because the duplicative voltages 134, 136 are the same, it can be difficult to establish a degree of rotation associated with each one.

Some embodiments of the present disclosure can determine the degree of rotation associated with the duplicative voltages 134, 136 based on an initial calibrated state. For instance, in some embodiments, the medical device 102 can be calibrated such that an initial degree of rotation of the elongate shaft 104 with respect to the elongate sheath 120 is known and/or is in a defined range of rotation. For example, the elongate shaft 104 can initially be set to an initial rotation state that is in a range between 45 degrees, which is associated with the first voltage minimum 132-1, and 315 degrees, which is associated with the fourth voltage minimum 132-4. Upon rotation of the elongate shaft 104 with respect to the elongate sheath 120 from the initial rotation state, if a voltage produced by the sheath sensor 122 is greater than the duplicative voltage 134, a determination can be made that the degree of rotation is associated with the first duplicative voltage 134, in an example.

Although the sheath sensor 122 is discussed as generating a particular voltage in response to the elongate shaft 104 being rotated with respect to the elongate sheath 120, a particular voltage can also be generated by the shaft sensor 116, which can be used to determine the degree of rotation of the elongate shaft 104 with respect to the elongate sheath 120. In some embodiments, a voltage model analogous to the voltage model 128 can be constructed for the shaft sensor 116 and used to determine the degree of rotation of the elongate shaft 104 with respect to the elongate sheath 120. For example, based on the variation of a coil voltage produced by the shaft sensor 116, the degree of rotation of the elongate shaft 104 with respect to the elongate sheath 120 can be determined.

FIG. 3A is a schematic cross-sectional side view of a dual sensor medical device 140 with magnetically permeable shaft strips 148-1, 148-2, 148-3, 148-4 of the same length and FIG. 3B is a cross-sectional end view of the dual sensor medical device depicted in FIG. 3A along line 3B-3B, in accordance with embodiments of the present disclosure. Although the present disclosure refers to a medical device 140, embodiments of the present disclosure can include two separate medical devices. For example, embodiments of the present disclosure can include an elongate shaft 142 (e.g., catheter) and an elongate sheath 152, further discussed herein. As discussed in relation to FIG. 2A, the medical device 140 can include an elongate shaft 142 that extends along a shaft longitudinal axis a-a and can include a shaft proximal end 144 and a shaft distal end 146. Although discussed as a shaft, the elongate shaft 142 can be a sheath or other type of medical device. The elongate shaft 142 can include one or more magnetically permeable shaft strips 148-1, 148-2, 148-3, 148-4 circumferentially disposed about the elongate shaft 142, as discussed in relation to FIG. 2A, which are hereinafter referred to in the plural as magnetically permeable shaft strips 148. However, in contrast to the magnetically permeable shaft strips depicted in FIG. 2A, the magnetically permeable shaft strips 148 in FIG. 2B can be of a same length. In some embodiments, the elongate shaft 142 can be hollow or solid and/or can include additional components. For example, the elongate shaft 142 can include items such as pull wires, conductors, optical fibers, etc.

In some embodiments, the proximal ends of each of the magnetically permeable shaft strips 148 can be located at a same longitudinal length along the shaft longitudinal axis a-a and the distal ends of each of the magnetically permeable shaft strips 148 can be located at a same longitudinal length along the shaft longitudinal axis a-a. In some embodiments, the proximal ends of each of the magnetically permeable shaft strips 148 and the distal ends of each of the magnetically permeable shaft strips 148 can be circumferentially disposed about and longitudinally staggered along the shaft longitudinal axis a-a.

In some embodiments, the elongate shaft 142 can include a shaft sensor 150 disposed along a portion of the particular shaft length along which the magnetically permeable shaft strips 148 are disposed. As discussed in relation to FIG. 2A, the shaft sensor 150 can be a wound coil in some embodiments, which can be wound around an outer surface of the elongate shaft 142 and along the shaft longitudinal axis b-b. In some embodiments, as depicted, the magnetically permeable shaft strips 148 can be disposed between an inner surface of the elongate shaft 142 and an inner surface of the shaft sensor 150. The magnetically permeable shaft strips 148 can be disposed along a particular portion of the elongate shaft 142.

In some embodiments, the shaft sensor 150 can surround the magnetically permeable shaft strips 148 and the particular portion of the elongate shaft 142. In some embodiments, the wound coil forming the shaft sensor 150 can extend from a proximal end of the magnetically permeable shaft strips 148 to a distal end of the magnetically permeable shaft strips 148, such that the wound coil envelops (e.g., is circumferentially wrapped around) the magnetically permeable shaft strips 148. In some embodiments, the wound coil forming the shaft sensor 150 can extend from a position that is located distally with respect to the distal ends of the magnetically permeable shaft strips 148 to a position that is located proximally with respect to the proximal ends of the magnetically permeable shaft strips 148. In some embodiments, the wound coil forming the shaft sensor 150 can extend from a position that is located proximally with respect to the distal ends of the magnetically permeable shaft strips 148 to a position that is located distally with respect to the proximal ends of the magnetically permeable shaft strips 148, such that the distal and proximal ends of the magnetically permeable shaft strips 148 are not enveloped by the shaft sensor 150.

As discussed in relation to FIG. 2A, embodiments of the present disclosure can include an elongate sheath 152 that extends along a sheath longitudinal axis, which can be generally parallel with the shaft longitudinal axis b-b and/or coincident with the shaft longitudinal axis b-b. The elongate shaft 152 can include a central lumen through which the elongate shaft 142 passes. In some embodiments, the elongate shaft 142 can be moved longitudinally through the central lumen of the elongate sheath 152 and/or rotated within the central lumen of the elongate sheath 152. The elongate sheath 152 can include a magnetically permeable sheath strip 154 disposed along a particular sheath length of the elongate sheath 152. In some embodiments, the magnetically permeable sheath strip 154 can have a length that is greater than or less than a length of the magnetically permeable shaft strips 148. In some embodiments, a sheath sensor 156 can be disposed along a portion of the particular sheath length. For example, the wound coil forming the sheath sensor 156 can extend from a proximal end of the magnetically permeable sheath strip 154 to a distal end of the magnetically permeable sheath strip 154.

In some embodiments, the wound coil forming the sheath sensor 156 can extend from a position that is located distally with respect to the distal ends of the magnetically permeable sheath strip 154 to a position that is located proximally with respect to the proximal ends of the magnetically permeable sheath strip 154. In some embodiments, the wound coil forming the sheath sensor 156 can extend from a position that is located proximally with respect to the distal ends of the magnetically permeable sheath strip 154 to a position that is located distally with respect to the proximal ends of the magnetically permeable sheath strip 154. In some embodiments, the magnetically permeable sheath strip 154 can be disposed between an inner surface of the elongate sheath 152 and an inner surface of the sheath sensor 156, as discussed in relation to FIG. 2A.

As discussed in relation to FIG. 2A, the sheath sensor 156 and/or shaft sensor 150 can be configured to detect a rotation of the elongate shaft 142 based on a rotation of the magnetically permeable shaft strips 148 relative to the magnetically permeable sheath strip 154. As the elongate shaft 142 is rotated with respect to the elongate sheath 152 in a direction of arrow 159, over the course of the rotation of the elongate shaft 142, each of the magnetically permeable shaft strips 148 can be aligned with the magnetically permeable sheath strip 154. As each one of the magnetically permeable shaft strips 148 is aligned with the magnetically permeable sheath strip 154, a mass of high permeability material becomes concentrated due to the radial alignment of one of the magnetically permeable shaft strips 148 with the magnetically permeable sheath strip 154. Thus, an increased concentration of magnetic flux can be delivered into the shaft sensor 150 and/or the sheath sensor 156. The increased concentration of magnetic flux delivered into the shaft sensor 150 and/or the sheath sensor 156 can cause an increased current generated within the coil winding of the shaft sensor 150 and/or sheath sensor 156, as depicted in FIG. 2C.

FIG. 3C is a graph that illustrates a coil voltage model 158 with respect to a rotation of a portion of the dual sensor medical device depicted in FIGS. 3A and 3B, in accordance with embodiments of the present disclosure. In some embodiments of the present disclosure, a particular roll of the elongate shaft 142 can be determined based on the coil voltage generated by the sheath sensor 156.

In contrast to FIG. 2A, each of the magnetically permeable shaft strips 148 can be of a same length, resulting in the same mass of material being placed within a proximity of the shaft sensor 150 and the sheath sensor 156 when each one of the magnetically permeable shaft strips 148 is radially aligned with the magnetically permeable sheath strip 154. Thus, while a current generated within the coil windings of the shaft sensor 150 and the sheath sensor 156 can vary, as depicted in FIG. 3C, when the elongate shaft 142 is rotated with respect to the elongate sheath 152, a voltage maximum generated by the shaft sensor 150 and the sheath sensor 156 can be the same in response to each of the magnetically permeable shaft strips 148 being radially aligned with the magnetically permeable sheath strip 154. For example, when the first magnetically permeable shaft strip 148-2 becomes radially aligned with the magnetically permeable sheath strip 154, a first coil voltage maximum 160-1 can be generated by the sheath sensor 156; when the second magnetically permeable shaft strip 148-2 becomes radially aligned with the magnetically permeable sheath strip 154, a second coil voltage maximum 160-2 can be generated by the sheath sensor 156; when the third magnetically permeable shaft strip 148-3 becomes radially aligned with the magnetically permeable sheath strip 154, a third coil voltage maximum 160-3 can be generated by the sheath sensor 156; and when the fourth magnetically permeable shaft strip 148-4 becomes radially aligned with the magnetically permeable sheath strip 154, a fourth coil voltage maximum 160-4 can be generated by the sheath sensor 156.

The first, second, third, and fourth coil voltage maximum 160-1, 160-2, 160-3, 160-4 can be the same with respect to one another because the magnetically permeable shaft strips 148 are of a same length. In some embodiments, a first coil voltage minimum 162-1, second coil voltage minimum 162-2, third coil voltage minimum 162-3, and fourth coil voltage minimum 162-4 can be generated as the elongate shaft 142 is rotated with respect to the elongate sheath 152. For example, the coil voltage minimums 162-1, 162-2, 162-3, 162-4 can be generated at degrees of rotation between those associated with the coil voltage maximums. For instance, coil voltage minimums can be generated when the elongate shaft 142 is rotated at approximately 45 degrees, 90 degrees, 225 degrees, and 315 degrees.

As discussed, the first, second, third, and fourth voltage coil maximums 160-1, 160-2, 160-3, 160-4 can be the same as one another and the first, second, third, and fourth coil voltage minimums 162-1, 162-2, 162-3, 162-4 can be the same as one another. Accordingly, while rotation of the elongate shaft 142 can be sensed, a directionality of the rotation may not be sensed. In some embodiments, one or more rotational encoders can be disposed on the shaft, such that a starting position and/or ending position of rotation can be determined. For example, one or more rotational encoders can be disposed on the shaft, which can be used to set an initial rotation of the shaft to 0 degrees, or another value. An encoder can be included between two of the magnetically permeable sheath strips, in some embodiments.

FIG. 4A is a schematic cross-sectional side view of a single sensor medical device 170 with variable length magnetically permeable shaft strips 172-1, 172-2, 172-3, 172-4 and FIG. 4B is a cross-sectional end view of the single sensor medical device 170 depicted in FIG. 4A along line 4B-4B, in accordance with embodiments of the present disclosure. Although embodiments of the present disclosure refer to a medical device 170, embodiments of the present disclosure can include two separate medical devices. For example, the medical device 170 can include an elongate shaft 174 (e.g., catheter) and an elongate sheath 180, further discussed herein. The single sensor medical device 170 can include an elongate shaft 174 that includes a proximal end 176 and a distal end 178. The elongate shaft 174 can extend along a shaft longitudinal axis c-c and can be hollow or solid. In some embodiments, the elongate shaft 174 can include items such as pull wires, conductors, optical fibers, etc. Embodiments of the present disclosure can include an elongate sheath 180, which includes a central lumen, through which the elongate shaft 174 can extend. The elongate sheath 180 can include a sheath sensor 182 and a magnetically permeable sheath strip 184. The magnetically permeable sheath strip 184 can be disposed along a particular sheath length of the elongate sheath 180 and the sheath sensor 182 can be disposed along a portion of the particular sheath length. In some embodiments, the single sensor medical device 170 can include the same features as the dual sensor medical device 102, as previously discussed, with the exception that the single sensor medical device 170 includes only a single sensor. For example, the single sensor medical device 170 can include a single sheath sensor 182 disposed along the portion of the particular sheath length and may not include a shaft sensor, as discussed in relation to FIG. 2A.

In some embodiments, sheath sensor 182 can produce a voltage in response to a rotation of the elongate shaft 174 in a direction of arrow 186 with respect to the elongate sheath 180, which can be modeled by a voltage model similar to or the same as voltage model 128. For example, as the elongate shaft 174 is rotated with respect to the elongate sheath 180, a different voltage maximum can be produced by the sheath sensor 182 as each one of the magnetically permeable shaft strips 172 passes within a close proximity and is aligned with the magnetically permeable sheath strip 184. In some embodiments, the magnetically permeable shaft strips 172 can be connected to the elongate shaft 174 by an adhesive. In some embodiments, the magnetically permeable shaft strips 172 can be disposed in an elongate lumen extending through a wall of the magnetically permeable shaft 174. As discussed herein, the elongate shaft 174 can be rotated with respect to the elongate sheath 180, causing each one of the magnetically permeable shaft strips 108 to be aligned with the magnetically permeable sheath strips 114, thus causing a mass of high permeability material to become concentrated due to the radial alignment of one of the magnetically permeable shaft strips 172 with the magnetically permeable sheath strip 184.

FIG. 5A is a schematic cross-sectional side view of a single sensor medical device 200 with magnetically permeable shaft strips 202-1, 202-2, 202-3, 202-4 that are of a same length and FIG. 5B is a cross-sectional end view of the single sensor medical device 200 depicted in FIG. 5A along line 5B-5B, in accordance with embodiments of the present disclosure. Although embodiments of the present disclosure refer to a medical device 200, embodiments of the present disclosure can include two separate medical devices. For example, embodiments of the present disclosure can include an elongate shaft 204 (e.g., catheter) and an elongate sheath 210, further discussed herein. The single sensor medical device 200 can include an elongate shaft 204 that includes a proximal end 206 and a distal end 208. The elongate shaft 204 can extend along a shaft longitudinal axis d-d and can be hollow or solid. In some embodiments, the elongate shaft 174 can include items such as pull wires, conductors, optical fibers, etc. Embodiments of the present disclosure can include an elongate sheath 210, which includes a central lumen, through which the elongate shaft 204 can extend. As previously discussed, the elongate shaft 204 can be solid or hollow and can include other items such as pull wires, conductors, optical fibers, etc. The elongate sheath 210 can include a sheath sensor 212 and a magnetically permeable sheath strip 214. The magnetically permeable sheath strip 154 can be disposed along a particular sheath length of the elongate sheath 210 and the sheath sensor 212 can be disposed along a portion of the particular sheath length. In some embodiments, the single sensor medical device 200 can include the same features as the dual sensor medical device 140, as previously discussed, with the exception that the single sensor medical device 200 includes only a single sensor. For example, the single sensor medical device 200 can include a single sheath sensor 212 disposed along the portion of the particular sheath length and may not include a shaft sensor, as discussed in relation to FIG. 3A.

In some embodiments, sheath sensor 212 can produce a voltage in response to a rotation of the elongate shaft 204 in a direction of arrow 216 with respect to the elongate sheath 210, which can be modeled by a voltage model similar to or the same as voltage model 158. For example, as the elongate shaft 204 is rotated with respect to the elongate sheath 210, a same voltage maximum can be produced by the sheath sensor 212 as each one of the magnetically permeable shaft strips 202 passes within a close proximity and is aligned with the magnetically permeable sheath strip 214. In some embodiments, the magnetically permeable shaft strips 202 can be connected to the elongate shaft 204 by an adhesive. In some embodiments, the magnetically permeable shaft strips 202 can be disposed in an elongate lumen extending through a wall of the elongate sheath 210. As discussed herein, the elongate shaft 204 can be rotated with respect to the elongate sheath 210, causing each one of the magnetically permeable shaft strips 202 to be radially aligned with the magnetically permeable sheath strip 214, thus causing a mass of high permeability material to become concentrated due to the radial alignment of one of the magnetically permeable shaft strips 202 with the magnetically permeable sheath strip 214.

FIG. 6A is a cross-sectional end view of a dual sensor medical device 218 with an equal number of magnetically permeable shaft strips 220-1, 220-2, 220-3, 220-4, hereinafter referred to in the plural as magnetically permeable shaft strips 220, and sheath strips 222-1, 222-2, 222-3, 222-4, hereinafter referred to in the plural as sheath strips 222, in accordance with embodiments of the present disclosure. Although embodiments of the present disclosure refer to a dual sensor medical device 218, embodiments of the present disclosure can include two separate medical devices. For example, embodiments of the present disclosure can include an elongate shaft 226 (e.g., catheter) and an elongate sheath 228, further discussed herein. In some embodiments, as previously discussed, one or more magnetically permeable shaft strips 220 can be disposed along a particular shaft length of the elongate shaft 226, which can be hollow or solid, and a shaft sensor 234 can be disposed along a portion of the particular shaft length. In some embodiments, one or more magnetically permeable sheath strips 222 can be disposed along the elongate sheath 228 and a sheath sensor 232 can be disposed along a portion of the particular sheath length. In some embodiments, the number of magnetically permeable shaft strips 220 can be equal to the number of magnetically permeable sheath strips 222 and can be radially aligned with one another, as depicted in FIG. 6A. Each of the magnetically permeable sheath strips 222 can be of the same longitudinal length and each of the magnetically permeable shaft strips 220 can be of varied longitudinal lengths and/or of the same longitudinal length.

In some embodiments, as the elongate shaft 226 is rotated with respect to the elongate sheath 228, each of the magnetically permeable shaft strips 220 can be radially aligned with one of the magnetically permeable sheath strips 222. Accordingly, each of the magnetically permeable sheath strips 222 can produce a coil voltage respective of each one of the magnetically permeable sheath strips 222 being radially aligned with each one of the magnetically permeable shaft strips 220. A same coil voltage can be produced by the sheath sensor 232 when each of the magnetically permeable shaft strips 220 are radially aligned with the magnetically permeable sheath strips 222 and are of a same longitudinal length. In some embodiments, a different coil voltage can be produced by the sheath sensor 232 when each of the magnetically permeable shaft strips 220 are radially aligned with the magnetically permeable sheath strips 222 and are of a different longitudinal length.

FIG. 6B is a cross-sectional end view of a single sensor medical device 240 with an equal number of magnetically permeable shaft strips 242-1, 242-2, 242-3, 242-4, hereinafter referred to in the plural as magnetically permeable shaft strips 242, and sheath strips 244-1, 244-2, 244-3, 244-4, hereinafter referred to in the plural as magnetically permeable sheath strips 244, in accordance with embodiments of the present disclosure. Although embodiments of the present disclosure refer to a single sensor medical device 240, embodiments of the present disclosure can include two separate medical devices. For example, embodiments of the present disclosure can include an elongate shaft 246 (e.g., catheter) and an elongate sheath 248, further discussed herein. In some embodiments, the single sensor medical device 240 can include the same features as the dual sensor medical device 218, with the exception that the single sensor medical device 240 does not include a shaft sensor, as discussed in relation to the dual sensor medical device 218. Upon rotation of the elongate shaft 246 with respect to the elongate sheath 248, each of the magnetically permeable shaft strips 242 can be radially aligned with one of the magnetically permeable sheath strips 244. Accordingly, the sheath sensor 250 can produce a coil voltage as a result of each one of the magnetically permeable sheath strips 244 being radially aligned with each one of the magnetically permeable shaft strips 242. A same coil voltage can be produced by the sheath sensor 250 when each of the magnetically permeable shaft strips 242 are radially aligned with the magnetically permeable sheath strips 244 and are of a same longitudinal length.

Figure 7A:
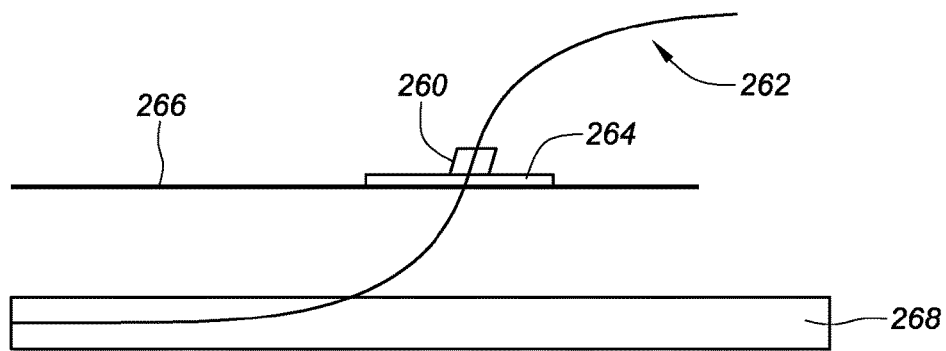
FIG. 7A is a cross-sectional side view of a trocar and a medical device inserted through the trocar and into a blood vessel, in accordance with embodiments of the present disclosure.

FIG. 7A is a cross-sectional side view of a trocar 260 and a medical device 262 inserted through the trocar and into a blood vessel, in accordance with embodiments of the present disclosure. In some embodiments, the trocar 260 can be used for introducing a medical device 262 into a body of a patient. For example, the trocar 260 can be connected with a patch 264. The patch can be used to connect the trocar 260 with a surface of a tissue 266. In some embodiments, a medical device 262 can be inserted through a central lumen defined by the trocar into the body, for example, into a blood vessel 268.

Figure 7B:
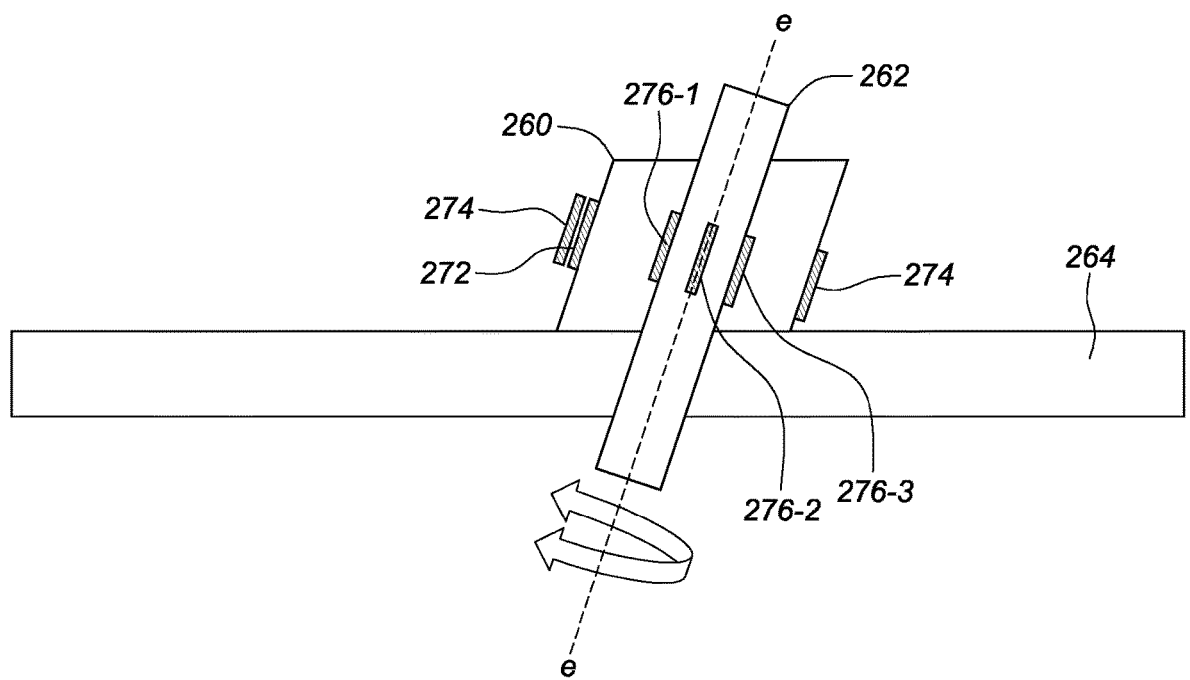
FIG. 7B is a cross-sectional magnified side view of the trocar and medical device depicted in FIG. 7A, in accordance with embodiments of the present disclosure.

In some embodiments, the trocar 260 can be configured to determine a rotation of the medical device 262, which in some embodiments can be an elongate shaft and/or sheath that is disposed about a longitudinal axis e-e, around which the medical device 262 can rotate. For example, as depicted in FIG. 7B, which is a cross-sectional magnified side view of the trocar and medical device depicted in FIG. 7A, the trocar 260 can act as a sheath, which can define a lumen through which the medical device 262 can be inserted. The trocar 260 can include the features such as those discussed herein. For example, the trocar 260 can include features such as those discussed in relation to FIGS. 2A to 6B and FIGS. 8A to 10B. For example, one or more magnetically permeable trocar (e.g., sheath) strips 272 can be disposed along a particular sheath length of the trocar 260, as discussed in relation to FIG. 5A. A trocar sensor 274 can be disposed along a portion of the particular sheath length of the trocar 260. In some embodiments, the medical device 262 can include one or more magnetically permeable strips 276-1, 276-2, 276-3 that are disposed along a portion of the medical device 262, as discussed in relation to FIG. 5A. A fourth magnetically permeable strip is hidden from view. As previously discussed, a coil voltage associated with the trocar sensor 274 can vary as the medical device 262 is rotated, thus allowing for a determination of a degree of rotation of the medical device 262 with respect to the trocar.

Figure 8A:
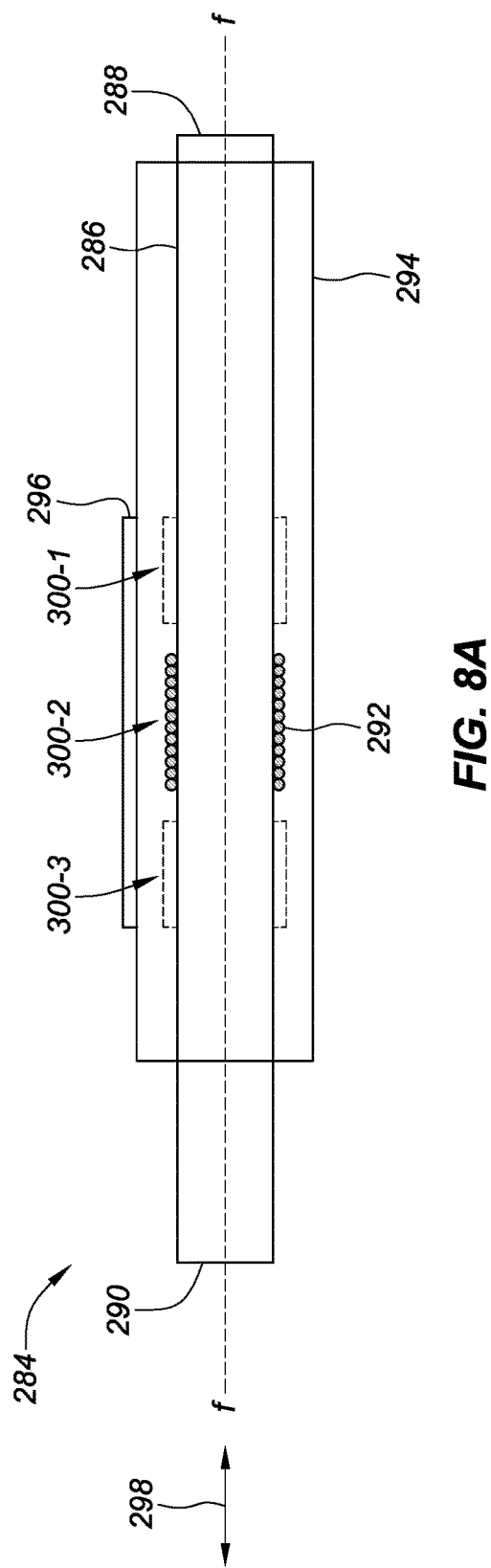
FIG. 8A is a partial cross-sectional side view of a single sensor medical device for sensing a linear movement of a portion of the medical device, in accordance with embodiments of the present disclosure.

FIG. 8A is a partial cross-sectional side view of a single sensor medical device 284 for sensing a linear movement of a portion of the medical device 284, in accordance with embodiments of the present disclosure. Although embodiments of the present disclosure refer to a single sensor medical device 284, embodiments of the present disclosure can include two separate medical devices. For example, embodiments of the present disclosure can include an elongate shaft 286 (e.g., catheter) and an elongate sheath 294, further discussed herein. In some embodiments, the elongate shaft 286 can extend along a shaft longitudinal axis f-f and can include a shaft proximal end 288 and a shaft distal end 290. Although the elongate shaft 286 is discussed as being a shaft herein, in some embodiments, the elongate shaft 286 can be a sheath or other type of elongate medical device. In some embodiments, a shaft sensor 292 can be disposed about the longitudinal axis f-f of the elongate shaft 286. An elongate sheath 294 can extend along a sheath longitudinal axis, which can be generally parallel with the shaft longitudinal axis f-f and/or coincident with the shaft longitudinal axis f-f. In some embodiments, the elongate shaft 286 can be moved longitudinally through the central lumen of the elongate sheath 294 and/or rotated within the central lumen of the elongate sheath 294. The elongate sheath 294 can have one or more magnetically permeable sheath strips 296 disposed along a particular sheath length of the elongate sheath 294. In some embodiments, the magnetically permeable sheath strips 296 can be disposed along the shaft longitudinal axis f-f.

The medical device 284 can be configured to determine a linear movement of a portion of the medical device 284. For example, the medical device 284 can be configured to determine a linear movement of the elongate shaft 286 with respect to the elongate sheath 294. The elongate sheath 294 can be used to guide the elongate shaft 286 to an intended destination, for example, within a body. The elongate shaft 286 can be linearly passed through the elongate sheath 286 in a direction of arrow 298. In some embodiments, as the elongate shaft 286 is passed through the elongate sheath 294, the shaft sensor 292 can pass the particular sheath length of the elongate sheath 294 and therefore be disposed within a close proximity to the magnetically permeable sheath strip 296. As depicted, the magnetically permeable sheath strip 296 can be located radially outward from the shaft sensor 292, causing a magnetic flux to be drawn through the magnetically permeable sheath strip 296. Thus, an increased concentration of magnetic flux can be delivered into the shaft sensor 292 upon alignment (e.g., radial alignment) of the shaft sensor 292 and the magnetically permeable sheath strip 296. As a result, a coil voltage generated by the shaft sensor 292 can be increased when the shaft sensor 292 passes under the magnetically permeable sheath strip 296 (e.g., is radially aligned with the magnetically permeable sheath strip), as depicted by a second centered position 300-2 of the shaft sensor 292 in FIG. 8A.

Figure 8B:
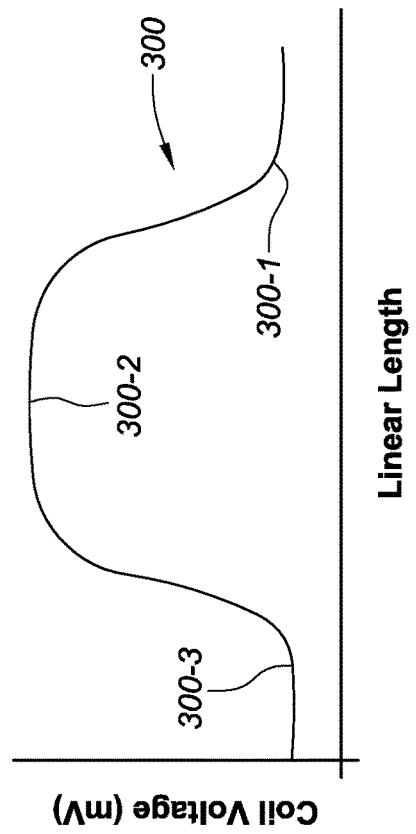
FIG. 8B is a graph that illustrates a linear coil voltage model with respect to a linear movement of a portion of the dual sensor medical device depicted in FIG. 8A, in accordance with embodiments of the present disclosure.

FIG. 8B is a graph that illustrates a linear coil voltage model 300 with respect to a linear movement of a portion of the dual sensor medical device depicted in FIG. 8A, in accordance with embodiments of the present disclosure. In some embodiments, as the elongate shaft 286 is pushed linearly with respect to the elongate sheath 294, a coil voltage produced by the shaft sensor 292 can be increased as the shaft sensor 292 becomes centered (e.g., longitudinally centered) under the magnetically permeable sheath strip 296. For example, as the elongate shaft 286 and the shaft sensor 292 is pushed from a first proximal position 300-1 and becomes aligned with a proximal end of the magnetically permeable sheath strip 296, a coil voltage produced by the shaft sensor 292 can start to increase from a first value, as shown by a first voltage at the first proximal position 300-1 in the coil voltage model 300. As the elongate shaft 286 and the shaft sensor 292 are pushed further proximally with respect to the first proximal position 300-1 to a second centered position 300-2 such that the shaft sensor 292 is centered between a proximal and distal end of the magnetically permeable sheath strip 296, the coil voltage produced by the shaft sensor 292 can be increased to a maximum value, as shown by the second voltage at the second centered position 300-2.

As the elongate shaft 286 and the shaft sensor 292 are pushed further proximally with respect to the second centered position 300-3 to a third distal position 300-3 such that the shaft sensor 292 becomes aligned with the distal end of the magnetically permeable sheath strip 296, the coil voltage produced by the shaft sensor 292 can decrease from the maximum value, as shown by the third voltage at the third distal position 300-3. In some embodiments, a linear position of the elongate shaft 286 with respect to the elongate sheath 294 can be determined based on a coil voltage produced by the elongate shaft sensor 292. For example, coil voltages produced by the elongate shaft sensor 292 can be associated with a linear position of the elongate shaft 286 and the associated shaft sensor 292.

FIG. 9A is a partial cross-sectional side view of a single sensor medical device for sensing a linear movement of a portion of the medical device 304 with a plurality of magnetically permeable sheath strips and FIG. 9B is a partial cross-sectional top view of a single sensor medical device for sensing a linear movement of a portion of the medical device 304 with a plurality of magnetically permeable sheath strips, in accordance with embodiments of the present disclosure. Although embodiments of the present disclosure refer to a single sensor medical device 304, embodiments of the present disclosure can include two separate medical devices. For example, embodiments of the present disclosure can include an elongate shaft 306 (e.g., catheter) and an elongate sheath 314, further discussed herein. The medical device 304 can include the same features of medical device 284 discussed in relation to FIGS. 8A to 8B, with the exception that the medical device 304 can include a plurality of magnetically permeable sheath strips 316-1, 316-2, 316-3. In some embodiments, an elongate shaft 306 with a proximal end 308 and a distal end 310 can include a shaft sensor 312 disposed about the longitudinal axis g-g of the elongate shaft 306 and along a particular shaft length of the elongate shaft 306, as previously discussed. Some embodiments can include an elongate sheath 314 extending along a sheath longitudinal axis and including a sheath proximal end and a sheath distal end. In some embodiments, the sheath longitudinal axis can be generally parallel or collinear with the shaft longitudinal axis g-g. In some embodiments, a plurality of magnetically permeable sheath strips can be longitudinally disposed along a particular sheath length of the elongate sheath.

In some embodiments, as the elongate shaft 306 is moved linearly in a direction of arrow 318, the shaft sensor 312 can be aligned with various ones of the magnetically permeable sheath strips 316-1, 316-2, 316-3. In an example, the shaft sensor 312 can be moved longitudinally past at least one of the magnetically permeable sheath strips 316-1, 316-2, 316-3. In some embodiments, each one of the magnetically permeable sheath strips 316-1, 316-2, 316-3 can be of a different longitudinal length, as depicted. For example, the magnetically permeable sheath strips 316-1, 316-2, 316-3 can be of an increasing length towards a distal end of the elongate sheath 314, as depicted in FIG. 9A, and/or a decreasing length towards a distal end of the elongate sheath 314. In some embodiments, the magnetically permeable sheath strips 316-1, 316-2, 316-3 can be of varied lengths and may not uniformly increase and/or decrease in size towards a distal end of the elongate shaft 306. In some embodiments, the magnetically permeable shaft strips can be of a uniform size. The plurality of magnetically permeable sheath strips 316-1, 316-2, 316-3 can be longitudinally spaced apart from one another, in some embodiments. For example, the plurality of magnetically permeable sheath strips 316-1, 316-2, 316-3 can be longitudinally spaced apart from one another by a uniform distance. In some embodiments, each of the plurality of magnetically permeable sheath strips 316-1, 316-2, 316-3 can be longitudinally spaced apart from one another by an increasing distance towards a distal end of the elongate sheath 314 and/or a decreasing distance towards a distal end of the elongate sheath 314.

In some embodiments, one or more of the plurality of magnetically permeable sheath strips 316-1, 316-2, 316-3 can be elongated and can extend along the sheath longitudinal axis. In some embodiments, the plurality of magnetically permeable sheath strips 316-1, 316-2, 316-3 can be elongated rectangles, as depicted in FIG. 9B. In some embodiments, the plurality of magnetically permeable sheath strips 316-1, 316-2, 316-3 can be planar squares, ovals, triangles, and/or circles of magnetically permeable material.

As the elongate shaft 306 and therefore the shaft sensor 312 is moved distally from a proximal position, the shaft sensor 312 can be aligned with a first magnetically permeable sheath strip 316-1 when in a first position 302-1, a second magnetically permeable sheath strip 316-2 when in a second position 302-2, and a third magnetically permeable sheath strip 316-3 when in a third position 302-3. As the shaft sensor 312 is aligned with each one of the magnetically permeable sheath strips 316-1, 316-2, 316-3 while in each one of the positions 302-1, 302-2, 302-3, a unique coil voltage can be induced in the shaft sensor 312. Accordingly, a linear position of the shaft sensor 312 and thus the elongate shaft 306 can be determined. In some embodiments, a different coil voltage can be induced in the shaft sensor 312 at each longitudinal position along the shaft longitudinal axis g-g. Thus, a longitudinal position of the shaft sensor 312 and thus the shaft 306 can be determined with respect to the elongate sheath 314. As previously discussed, duplicative voltages can be induced in the shaft sensor 312 at different positions along the longitudinal axis. However, as discussed herein, the medical device 304 can be calibrated such that an initial linear position of the elongate shaft 306 with respect to the elongate sheath 314 is known and/or within a defined range of linear movement. Based on initial voltages induced in the shaft sensor 312 and the initial linear position, a linear movement of the shaft sensor 312 with respect to the elongate sheath 314 can be determined.

Figure 10A:
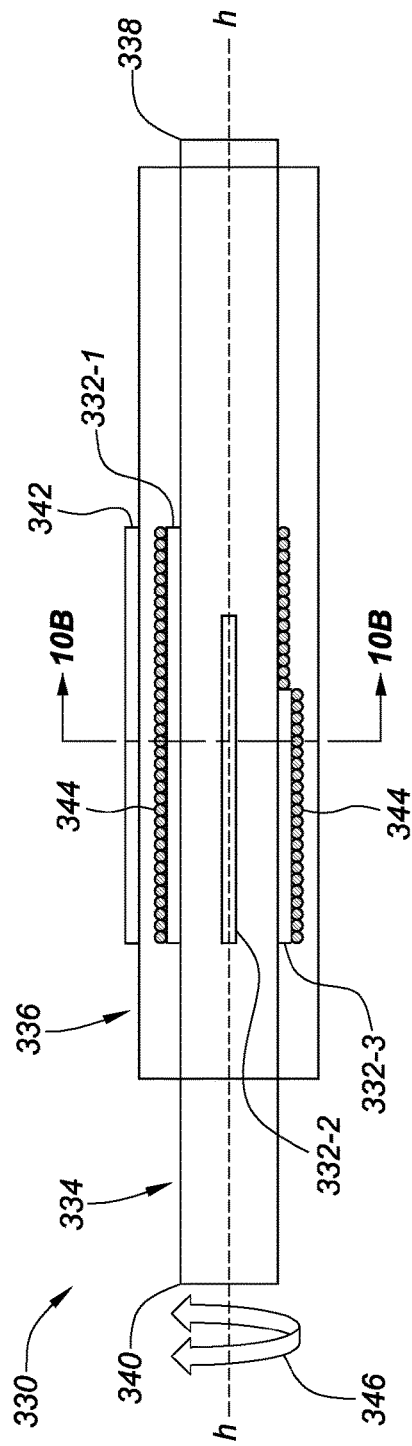
FIG. 10A is a schematic side view of a single sensor medical device with variable length magnetically permeable shaft strips, in accordance with embodiments of the present disclosure.
Figure 10B:
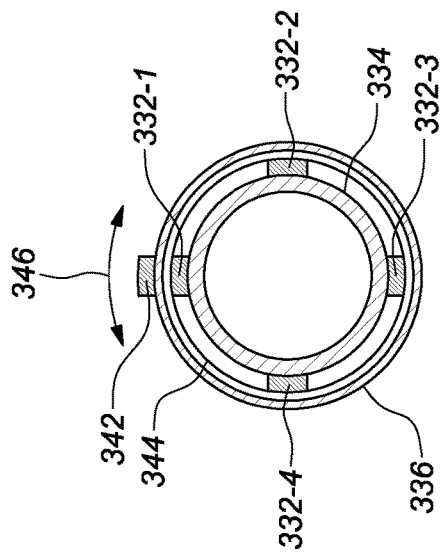
FIG. 10B is a cross-sectional end view of the dual sensor medical device depicted in FIG. 10A along line 10B-10B, in accordance with embodiments of the present disclosure.

FIG. 10A is a schematic side view of a single sensor medical device 330 with variable length magnetically permeable shaft strips 332-1, 332-2, 332-3, 333-4 and FIG. 10B is a cross-sectional end view of the single sensor medical device 330 depicted in FIG. 10A along line 10B-10B, in accordance with embodiments of the present disclosure. The single sensor medical device 330 can include those features as discussed in relation to FIG. 2A, with the exception of a sheath sensor 122. Although the present disclosure refers to a medical device 330, embodiments of the present disclosure can include two separate medical devices. For example, embodiments of the present disclosure can include an elongate shaft 334 (e.g., catheter) and an elongate sheath 336, further discussed herein. In some embodiments, the elongate shaft 334 can extend along a shaft longitudinal axis h-h and can include a shaft proximal end 338 and a shaft distal end 340. Although the elongate shaft 334 (e.g., catheter) is discussed as being a shaft herein, in some embodiments, the elongate shaft 334 can be a sheath or other type of elongate medical device. In some embodiments, the shaft 334 can be hollow or solid and/or can include additional components. For example, the shaft 334 can include items such as pull wires, conductors, optical fibers, etc.

In some embodiments, one or more magnetically permeable shaft strips 332-1, 332-2, 332-3, 332-4 can be disposed along a particular shaft length of the elongate shaft 334 and are hereinafter referred to in the plural as magnetically permeable shaft strips 332. The elongate shaft 334 includes a fourth magnetically permeable shaft strip 332-4, which is further depicted in FIG. 10B. As discussed in relation to FIG. 2A, the elongate shaft 334 can include fewer than or greater than four magnetically permeable shaft strips 332, in some embodiments. In an example, the magnetically permeable shaft strips 332 can be circumferentially disposed about the elongate shaft 334. Each of the magnetically permeable shaft strips 332 can be of a different length, as depicted. However, as discussed herein, for example in relation to FIG. 3A, the magnetically permeable shaft strips 332 can be of a same length.

Embodiments of the present disclosure can include an elongate sheath 336 that extends along a sheath longitudinal axis. In some embodiments, the sheath longitudinal axis can be generally parallel with the shaft longitudinal axis a-a and/or coincident with the shaft longitudinal axis h-h. The elongate sheath 336 can include a central lumen through which the elongate shaft 334 is configured to pass. In some embodiments, the elongate shaft 334 can be moved longitudinally through the central lumen of the elongate sheath 336 and/or rotated within the central lumen of the elongate sheath 336.

The elongate sheath 336 can include a magnetically permeable sheath strip 342 disposed along a particular sheath length of the elongate sheath 336. In some embodiments, the magnetically permeable sheath strip 342 can have a length that is greater than, equal to, or less than a length of the longest magnetically permeable shaft strip 332. As previously discussed, the elongate sheath 336 may not include a shaft sensor. Although one magnetically permeable sheath strip 342 is included on the elongate sheath 336, the elongate sheath 336 can include a plurality of magnetically permeable sheath strips, for example, as discussed in relation to FIGS. 6A and 6B. In contrast to FIGS. 6A and 6B, however, the elongate sheath 336 depicted in FIGS. 10A and 10B may not include a sheath sensor.

As each one of the magnetically permeable shaft strips 332 is aligned with the magnetically permeable sheath strip 342, a mass of high permeability material becomes concentrated due to the alignment of the two magnetically permeable strips. Thus, an increased concentration of magnetic flux can be delivered into the shaft sensor 344. The increased concentration of magnetic flux delivered into the shaft sensor 344 can cause an increased current to be generated within the coil winding of the shaft sensor 344 as previously discussed herein. Accordingly, a rotation of the elongate shaft in the direction of arrow 346 with respect to the elongate sheath can be determined based on the variation in current generated by the shaft sensor 344. In some embodiments, the elongate shaft 334 (e.g., catheter) and the elongate sheath 336 (e.g., introducer) can be included in a kit. In some embodiments of the present disclosure, the respective elongate shafts (e.g., catheters) and the elongate sheaths (e.g., introducers) discussed in relation to FIGS. 2A to 9B can also be included in respective kits.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment of a medical device sensor has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter comprising:
    an elongate shaft extending along a shaft longitudinal axis and including a shaft proximal end and a shaft distal end; and
    a plurality of magnetically permeable shaft strips disposed along a shaft length of the elongate shaft, wherein:
        the plurality of magnetically permeable shaft strips are circumferentially spaced apart from one another; and
        the magnetically permeable shaft strips longitudinally extend along the elongate shaft.

2. The catheter of claim 1, wherein a longitudinal length of each one of the plurality of magnetically permeable shaft strips is the same with respect to one another.

3. The catheter of claim 2, wherein the elongate shaft includes a shaft sensor disposed along a portion of the shaft length.

4. The catheter of claim 3, wherein the plurality of magnetically permeable shaft strips are disposed between an inner surface of the elongate shaft and an inner surface of the shaft sensor.

5. The catheter of claim 3, wherein the shaft sensor includes a coil extending along and disposed about the shaft longitudinal axis.

6. The catheter of claim 5, wherein the coil is disposed along the longitudinal length of each one of the plurality of magnetically permeable strips.

7. The catheter of claim 5, wherein each of the plurality of magnetically permeable strips are disposed between the coil and an exterior of the elongate shaft.

8. The catheter of claim 5, wherein each of the plurality of magnetically permeable strips are disposed between the sensor coil and an exterior of the elongate shaft.

9. The catheter of claim 1, wherein the magnetically permeable shaft strips are formed from a metallic glass alloy.

10. The catheter of claim 1, wherein a longitudinal length of each of the plurality of magnetically permeable shaft strips decreases in a first circumferential direction.

11. The catheter of claim 10, wherein a distal end of each of the magnetically permeable shaft strips is disposed at a same longitudinal length along the shaft longitudinal axis.

12. The catheter of claim 1, wherein a circumferential spacing between each one of the plurality of magnetically permeable shaft strips is equal.

13. A catheter comprising:
    an elongate shaft extending along a shaft longitudinal axis and including a shaft proximal end and a shaft distal end;
    a plurality of magnetically permeable shaft strips disposed along a shaft length of the elongate shaft, wherein:
        the plurality of magnetically permeable shaft strips are circumferentially spaced apart from one another; and
        the magnetically permeable shaft strips longitudinally extend along the elongate shaft; and
    a sensor coil disposed along a portion of the shaft length.

14. The catheter of claim 13, wherein the magnetically permeable shaft strips are formed from a mu-metal.

15. The catheter of claim 13, wherein each of the plurality of magnetically permeable shaft strips are circumferentially spaced apart from one another by a same distance.

16. The catheter of claim 13, wherein each of the plurality of magnetically permeable shaft strips are circumferentially spaced apart from one another by a different distance.

17. A catheter comprising:
    an elongate shaft extending along a shaft longitudinal axis and including a shaft proximal end and a shaft distal end;
    a plurality of magnetically permeable shaft strips disposed along a shaft length of the elongate shaft, wherein:
        the plurality of magnetically permeable shaft strips are circumferentially spaced apart from one another; and
        the magnetically permeable shaft strips longitudinally extend along the elongate shaft; and
    a sensor coil disposed along a portion of the shaft length, wherein the magnetically permeable shaft strips are disposed radially inward of the sensor coil.

18. The catheter of claim 17, wherein each one of the magnetically permeable shaft strips is formed from a plurality of traces.

19. The catheter of claim 17, wherein the elongate shaft defines a plurality of lumens longitudinally extending through a wall of the catheter shaft.

20. The catheter of claim 19, wherein each of the plurality of magnetically permeable shaft strips is disposed in one of the plurality of lumens.

* * * * *